United States Patent [19]

Natwick et al.

[11] Patent Number: 5,116,203

[45] Date of Patent: May 26, 1992

[54] DETECTING OCCLUSION OF PROXIMAL OR DISTAL LINES OF AN IV PUMP

[75] Inventors: Vernon R. Natwick, Los Altos; Michael W. Lawless, Poway; Joseph E. Doll, Saratoga; Chung-You C. Wu, San Francisco, all of Calif.

[73] Assignee: Abbott Laboratories, Abbott Park, Ill.

[21] Appl. No.: 743,559

[22] Filed: Aug. 12, 1991

Related U.S. Application Data

[63] Continuation-in-part of Ser. No. 494,210, Mar. 15, 1990, Pat. No. 5,055,001.

[51] Int. Cl.⁵ .................... F04B 43/12; F04B 49/02
[52] U.S. Cl. ........................... 417/53; 417/63; 417/282; 417/474; 604/153
[58] Field of Search ............. 417/53, 63, 282, 474, 417/479, 559, 510; 604/153

[56] References Cited

U.S. PATENT DOCUMENTS 4,453,931  6/1984  Pastrone ............... 417/510 X
4,836,752  6/1989  Burkett ................. 417/479 X Primary Examiner—Stephen M. Hepperle
Attorney, Agent, or Firm—Christensen, O'Connor, Johnson & Kindness

[57] ABSTRACT

A method and apparatus for detecting proximal and distal occlusions of flexible tubing in a positive displacement pump. A volumetric pump (30) includes a motor (146) that rotatably drives a cam assembly (142). The rotating cam assembly actuates a plunger (48), causing it to compress a pumping portion (34b) of a flexible tubing (34), compression of the tubing displaces fluid trapped within the pumping portion, causing it to flow past an outlet cracking valve (52). A proximal pressure sensor (44) and a distal pressure sensor (56) each produce signals indicative of the pressure within the proximal portion and distal portion of the flexible tubing, which are used to determine whether a proximal or distal occlusion of the flexible tubing has occurred. Both pressure sensors comprise strain gauges connected to flexures that apply a spring-biased force against the proximal and distal portions of the flexible tubing. These sensors thereby respond to the cross-sectional size (diameter) of the tubing, as affected by fluid pressure therein. Proximal and distal pressures are thus monitored without violating the integrity of the flexible tubing passing through the volumetric pump.

24 Claims, 17 Drawing Sheets

DETECTING OCCLUSION OF PROXIMAL OR DISTAL LINES OF AN IV PUMP

RELATED APPLICATIONS

This application is a continuation-in-part of pending commonly assigned prior U.S. patent application, Ser. No. 494,210, filed Mar. 15, 1990 now U.S. Pat. No. 5,055,001. The benefit of the filing date of this prior application is hereby claimed under 35 U.S.C. § 120.

FIELD OF THE INVENTION

This invention generally pertains to apparatus and a method for detecting an occlusion of a line carrying fluid, and more specifically, for detecting the occlusion of a line carrying fluid into or out of a pump.

BACKGROUND OF THE INVENTION

Occlusion of the lines carrying fluid into the inlet of a pump or out its discharge port is normally readily evident—fluid delivery from the pump ceases or at least, is reduced. Of course, the cessation of fluid flow from a pump discharge line can also be caused by other faults, such as a failure of the pump or interruption of its power supply. In certain applications, it may be important to determine whether an occlusion of the inlet or outlet line interrupted the fluid flow, so that appropriate steps can be taken to correct the problem.

Maintenance of fluid flow from a pump may be critical, particularly in the field of medical technology in which pumps are often employed in procedures performed upon a patient. For example, interruption of the intravenous infusion of drugs into a patient's vascular system using a peristaltic, cassette, or other type of pump can have serious consequences that may endanger the patient's health. It is therefore very important that medical personnel be quickly alerted if such an interruption occurs. More importantly, to ensure that the appropriate corrective response is taken, the cause of the interruption in fluid flow should be identified. If an occlusion of the inlet (proximal) line connecting the source of the medicinal fluid to the pump inlet occurs, the monitoring system should identify that cause of the interruption; similarly, any occlusion of the outlet (distal) line connecting the pump discharge port to the patient should also be specifically identified.

One way to detect an occlusion of a proximal or distal fluid line is to monitor fluid flow in the line. Most devices for monitoring fluid flow must be installed in the line so that the fluid mechanically interacts with a flow sensor as the fluid moves through the device. However, in the case of peristaltic pumps and other types of pumps that are intended to pump fluid through an integral tube set, it is undesirable to install such flow sensors, since the installation requires cutting into the tube set on both the proximal and distal sides of the pump to insert flow in-line sensors. Instead, it is preferable to detect any occlusion of either the proximal or distal lines with a device that is installed on an integral tube set, much like a peristaltic pump. Even more preferable is an occlusion detector that is incorporated into the pump so that it does not require separate installation on the proximal and/or distal lines.

Another problem with using a conventional flow detector to determine when an occlusion has occurred is that the restriction of the line may be only partial, allowing fluid flow to continue at a reduced rate that is insufficient to trigger an alarm. If a patient rolls over onto the distal line, pinching the IV line partially closed, fluid flow through the line may be only reduced, yet the patient does not receive the prescribed dosage of the medication. The reduced flow rate caused by the restriction of the distal line may severely limit the total dose delivered during a predefined interval.

If the flow of a medicinal fluid to a patient is sufficiently reduced by a pinched distal line, pressure upstream of the flow can build so that if the occlusion of the delivery line is then removed, a potentially dangerous bolus of medicinal fluid is delivered to the patient. Accordingly, an occlusion detector should be responsive to pressure in the distal line.

Equally important in the detection of such an occlusion is avoidance of false alarms. A momentary interruption of fluid flow should not trigger an occlusion alarm, since the short term interruption of fluid flow probably has no serious detrimental consequences. Similarly, variations in the environmental conditions that might affect the detection of an occlusion should be ignored or filtered out to avoid false alarms. If the occlusion detector produces false alarms, the alarms will eventually be ignored, potentially causing a serious reduction in fluid flow to remain uncorrected.

It will therefore be apparent that a device and a method are required for detecting an occlusion of either a distal or proximal line of a pump and particularly, an occlusion of the distal or proximal line of an IV pump used to administer medical fluid to a patient. The advantages of the present invention in this regard will be apparent from the attached drawings and from the Description of the Preferred Embodiments of the Invention that follows.

SUMMARY OF THE INVENTION

In accordance with the present invention, apparatus are provided to detect an occlusion of either an inlet line or an outlet line of a pump. The apparatus comprises a first pressure sensor that is mechanically coupled to the inlet line to sense a fluid pressure therein without exposure to the fluid within the inlet line, producing a first signal indicative of that fluid pressure. Similarly, a second pressure sensor is mechanically coupled to the outlet line to sense a fluid pressure therein, without exposure to the fluid within the outlet line and is operative to produce a second signal indicative of that fluid pressure. Control means, which are connected to receive the first and the second signal, monitor the fluid pressure within the inlet and the outlet lines and include detection means for determining whether an occlusion of the inlet line or of the outlet line has occurred, as a function of the first and the second signals.

The first and second pressure sensors each comprise strain gauges that respond to a cross-sectional deflection of the inlet and the outlet lines, respectively, caused by the fluid pressure within the lines. The first signal and the second signal that are produced by the strain gauges correspond to the deflection and thus, to the fluid pressures within the inlet and the outlet lines.

The control means determine a baseline pressure for the inlet line and a baseline pressure for the outlet line, based upon a weighted average of the fluid pressure therein, as sensed at predetermined times during consecutive pump cycles to compensate for variations in the deflection of the inlet line and the outlet line that are independent of an occlusion. The detection means detect an occlusion of the inlet line if the fluid pressure within the inlet line deviates from its baseline pressure by more than a predefined amount during a predefined number of consecutive pump cycles. In the same manner, the detection means detect an occlusion of the outlet line if the fluid pressure within the outlet line deviates from its baseline pressure by more than a predefined amount during a predefined number of consecutive pump cycles.

The detection means determine a pressure delta baseline that is a function of a difference between the baseline pressures of the inlet line and the outlet line and use the pressure delta baseline as a reference in determining whether an absolute occlusion of the outlet line has occurred. Included in the control means are memory means for storing the pressure delta baseline. The detection means compare a present value of the pressure delta baseline with a previous value of the pressure delta baseline that was stored by the memory means to detect the absolute occlusion of the outlet line.

Interface means are provided to enable an operator to select a reference pressure used by the detection means in detecting an occlusion of the inlet line or the outlet line. The detection means compensate for changes in the cross-sectional deflection of the inlet line and of the outlet line over time, due to changes in an elasticity of the lines under pressure.

A method for detecting an occlusion of either an inlet line or of an outlet line of a pump is a further aspect of this invention. The method includes steps that are generally consistent with the functions carried out by the elements of the apparatus discussed above.

DETAILED DESCRIPTION OF THE PREFERRED EMBODIMENT

Volumetric Pump

The term "volumetric pump" is applied to a pump in which the present invention is used, because the term appropriately emphasizes one of the pump's more important advantages. Specifically, during each pumping stroke, the volumetric pump consistently and repeatedly displaces a defined volume of fluid at a defined pressure, thereby ensuring that a desired rate of fluid flow is accurately delivered by the pump. By providing consistency in the force required to drive the pump throughout the pumping cycle, the present invention helps to insure that the desired flow rate is accurately produced.

Figure 1:
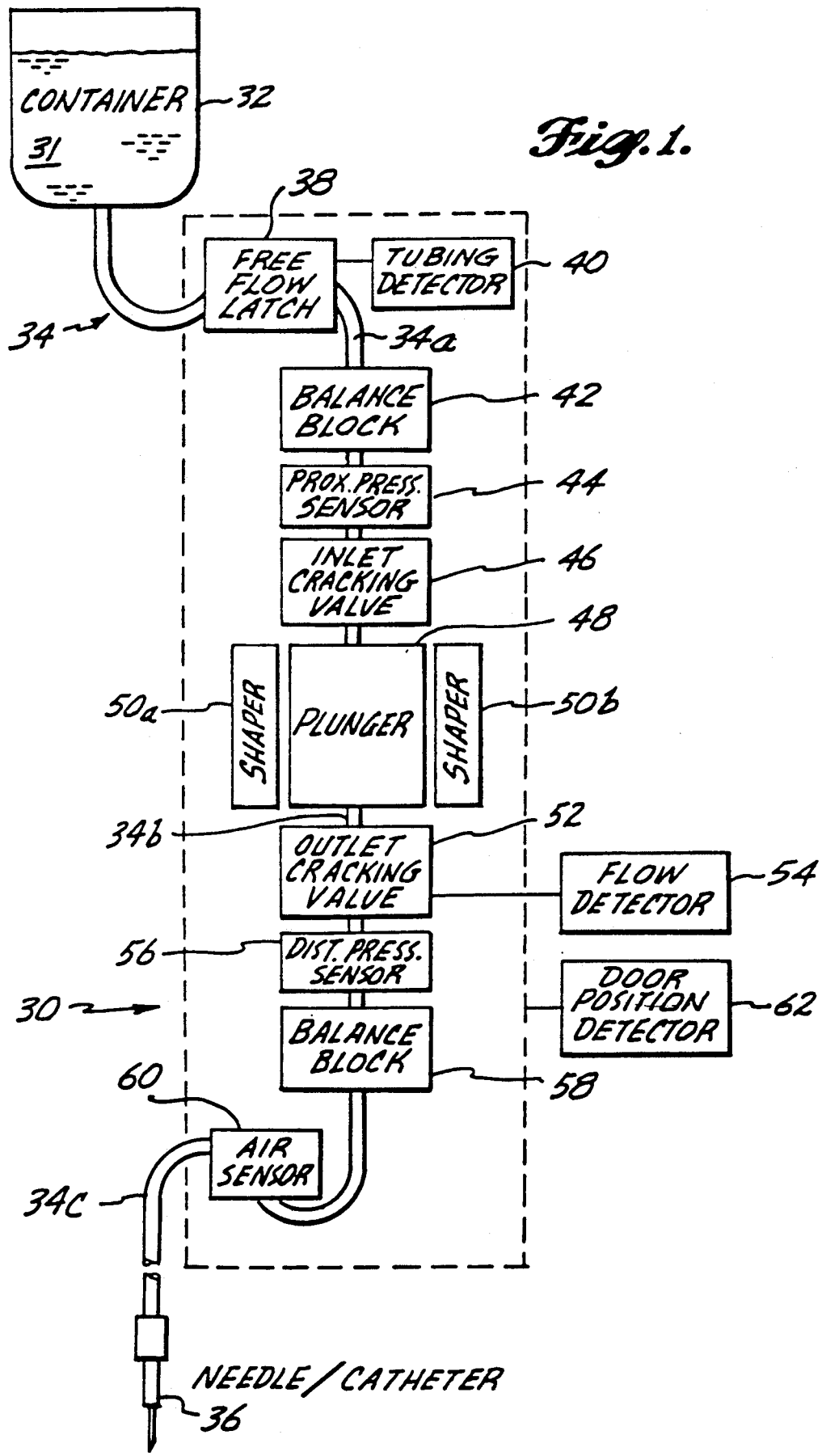
FIG. 1 is a schematic block diagram of a volumetric pump in which the present invention is used.

In FIG. 1, a volumetric pump that includes the present invention is generally illustrated in a block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 flowing from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, it comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 is inhibited if the signal indicates that the flexible tubing is not in place.

A balance block 42 rests against proximal portion 34a of flexible tubing 34 and serves to compensate for variations or changes in the elasticity of flexible tubing 34. The function and operation of balance block 42 are more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of flexible tubing 34 for use in monitoring the operation of the pump and to determine if proximal portion 34a has become occluded, in accordance with the present invention.

A key element in the operation of volumetric pump 30 is an inlet cracking valve 46, disposed immediately downstream of proximal pressure sensor 44. Inlet cracking valve 46 functions in cooperation with a plunger 48 and an outlet cracking valve 52, which are disposed sequentially downstream of the inlet cracking valve, to provide the displacement of a volumetric quantity of fluid from pumping portion 34b of the flexible tubing by volumetric pump 30 and to generally isolate the volumetric pump from variations in proximal and distal fluid pressure, due, for example, to variations in the elevation of container 32, or variations in the back pressure of fluid in distal portion 34c of the flexible tubing. A flow detector 54 is interconnected with outlet cracking valve 52 and produces a signal indicating whether fluid is successfully being pumped by volumetric pump 30 into distal portion 34c. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A further element of the occlusion detector is a distal pressure sensor 56, which produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of distal portion 34c of the flexible tubing.

Immediately adjacent distal pressure sensor 56 is a balance block 58. Cooperating with outlet cracking valve 52, balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume in the fluid discharged from the volumetric pump, and produces a signal indicative of such air bubbles, which stops volumetric pump 30 and initiates an alarm to prevent a potentially harmful air embolism forming in the fluid being introduced into a patient through needle/catheter 36. Air sensor 60 comprises a generally conventional piezoelectric ultrasonic transmitter and receiver (not separately shown), spaced apart on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble. The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

Figure 2:
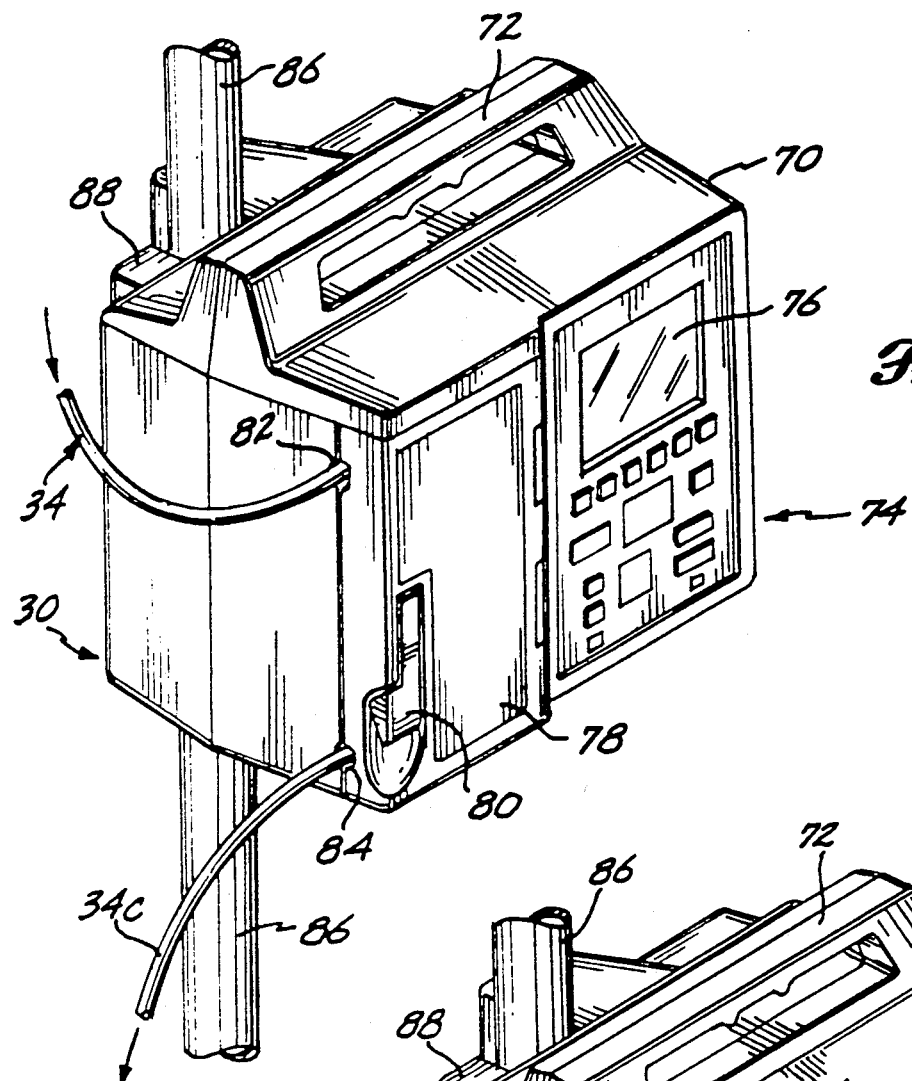
FIG. 2 is an isometric view of the volumetric pump, showing an access door that is closed and latched in place, securing a flexible tube within the pump.
Figure 3:
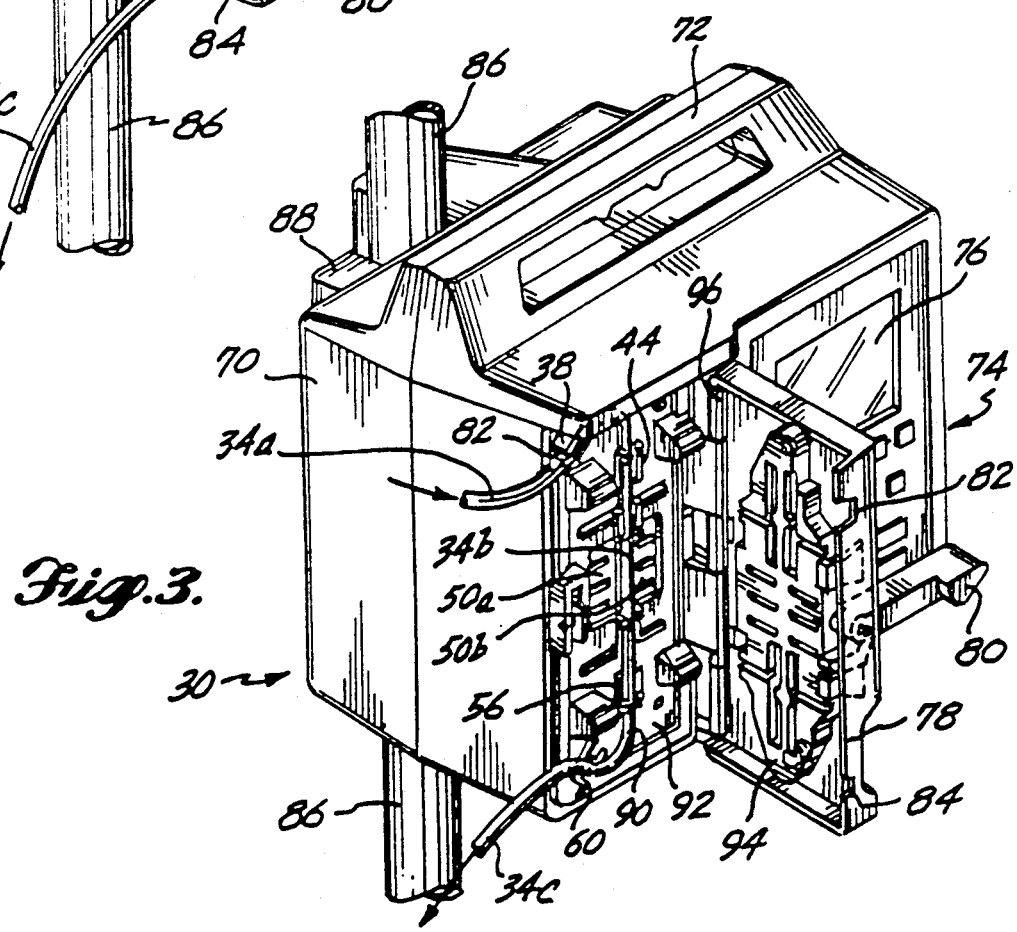
FIG. 3 is an isometric view, similar to that shown in FIG. 2, but with the access door shown in an open position, so as to disclose the path followed by the flexible tube through the volumetric pump.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump. Certain data entered by the operator define parameters relating to the detection of an occlusion of the proximal or distal portions 34a, 34c of the flexible tubing, as explained below.

On the back of housing 70 is formed a clamp 88, which is used to removably attach volumetric pump 30 to a post 86, for example at the bedside of a patient. Details of clamp 88 are not shown since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly so that door 78 can be swung open on a hinge 96, giving access to an inner cover 92 that defines the path followed by flexible tubing 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84, formed in the lower side portion of door 78, overlies distal portion 34c of the flexible tubing. A pressure plate 94 disposed on the inner surface of door 78 comes into contact with flexible tubing 34 along the length of channel 90 as door 78 is closed and latched with handle 80. The integrity of flexible tubing 34 is thus maintained when volumetric pump 30 is used to administer medication to a patient, since it is not necessary to cut into the flexible tubing to install the pump prior to its operation. Similarly, the detection of an occlusion of proximal portion 34a or distal portion 34c is accomplished without requiring installation of any separate apparatus and without violating the integrity of the flexible tubing. Volumetric pump 30 thus provides the characteristic ease of use of a conventional peristaltic pump, with the relatively greater accuracy of a cassette pump. Integration of occlusion detection within the pump provides a significant safety feature not generally available on other types of pumps.

Figure 4:
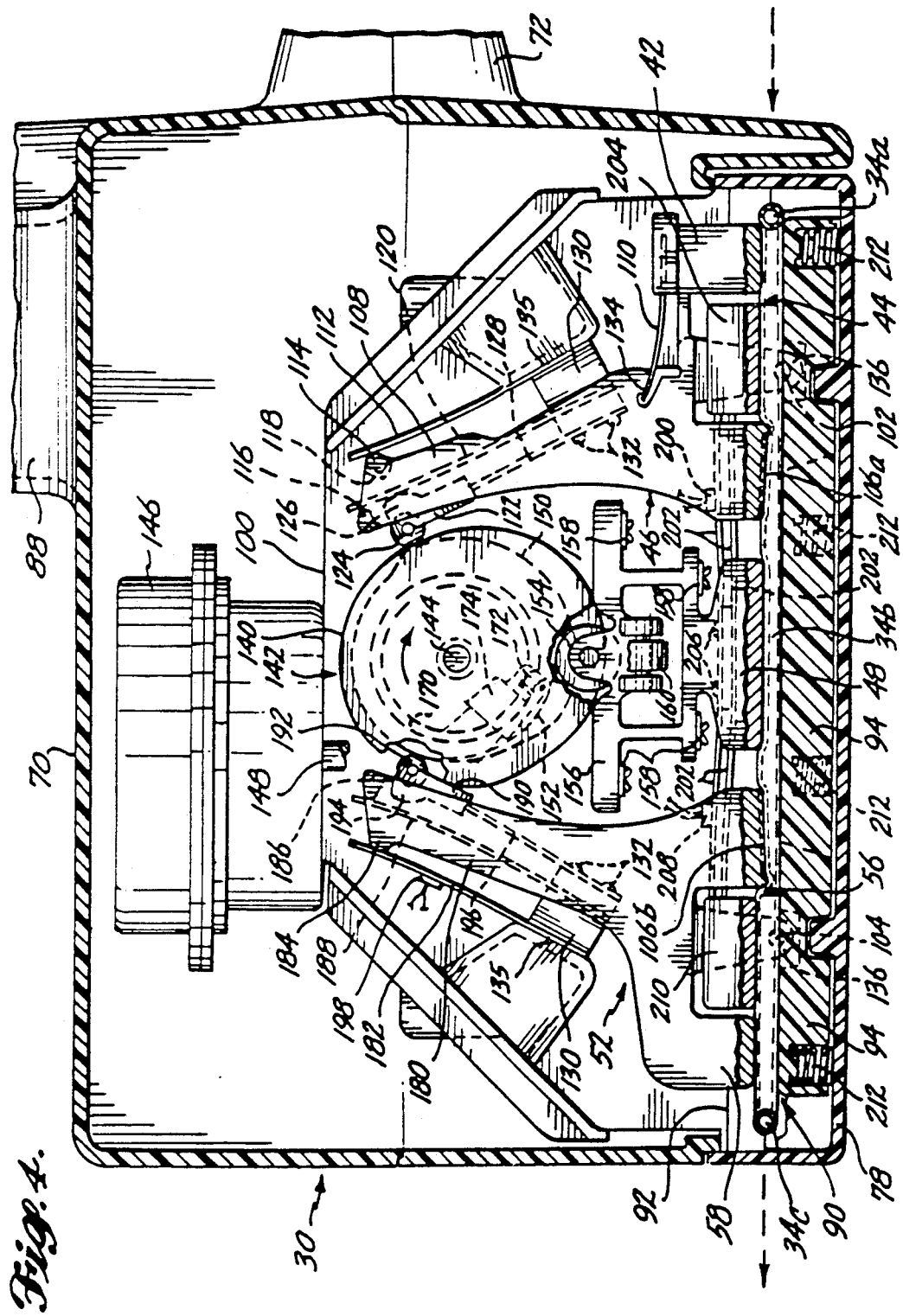
FIG. 4 is a longitudinal cross section of the pump assembly shown in FIGS. 2 and 3.
Figure 5:
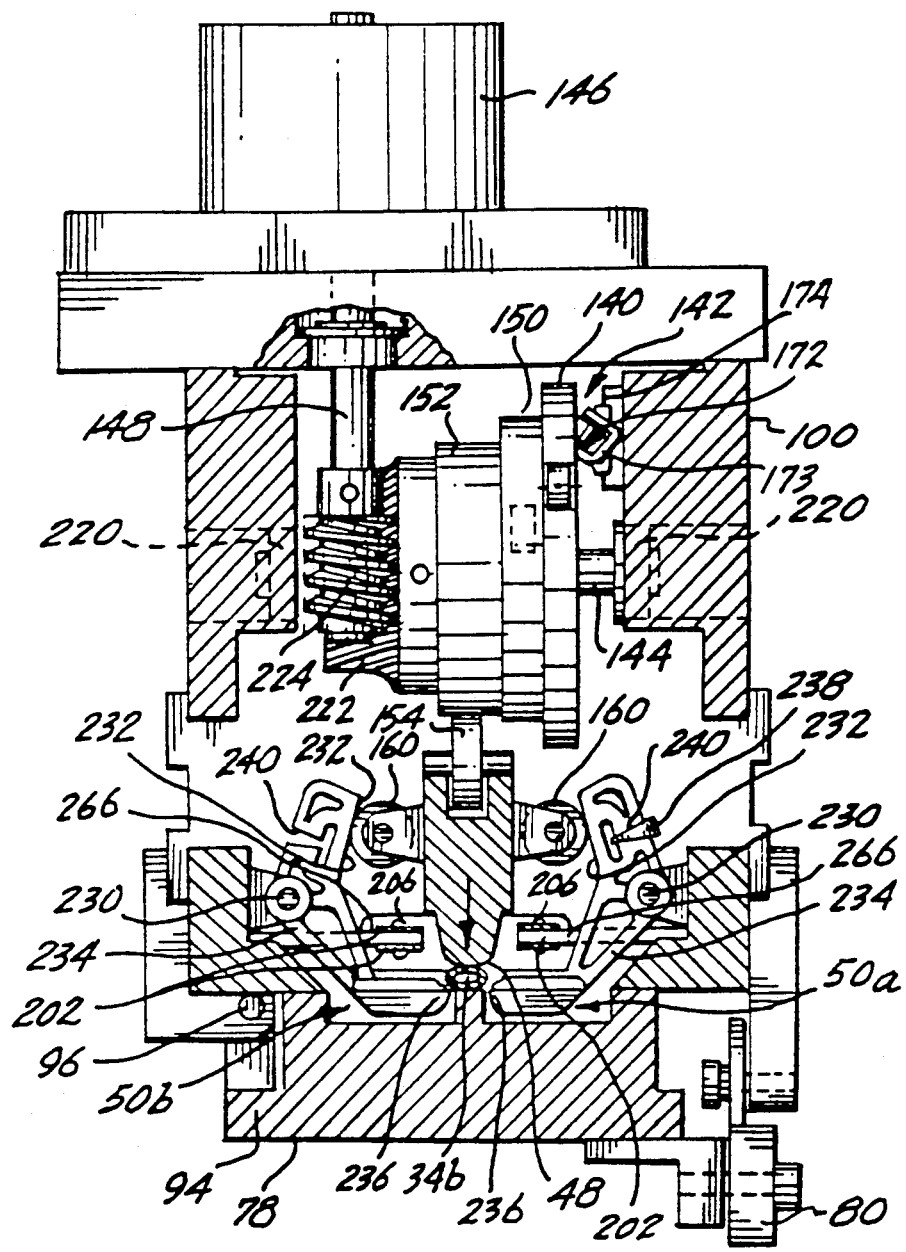
FIG. 5 is a schematic transverse cross section of the volumetric pump, illustrating the first embodiment of the present invention.
Figure 6:
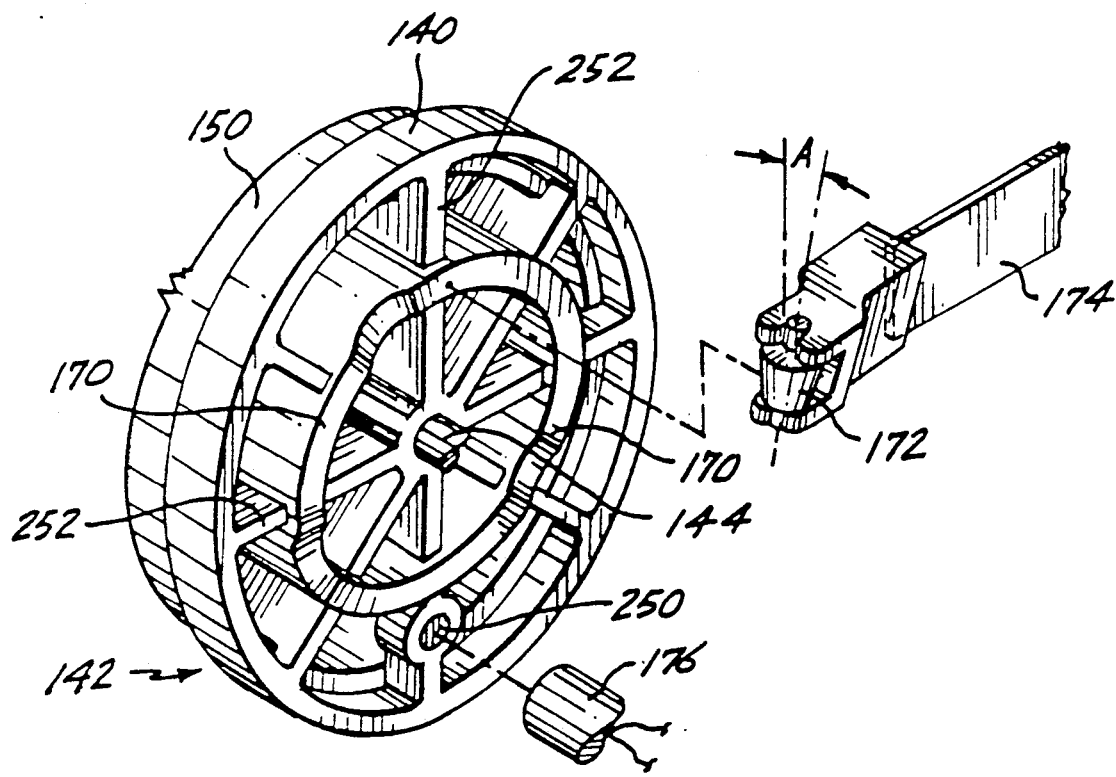
FIG. 6 is an isometric view of one end of a portion of the cam assembly on which a torque compensation track is disposed.

FIGS. 4, 5, and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212. Springs 212 bias pressure plate 94 away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type peristaltic pumps, as will be apparent from the following disclosure.

An inlet valve arm 108 extends upwardly from valve face 106a on inlet cracking valve 46. Disposed generally above inlet cracking valve pivot mounts 102 are flat metal spring flexures 110, which connect balance block 42 to a slot 134, formed on the back side of inlet valve arm 108. Flexures 110 are snapped within slot 134 and flex to enable inlet valve arm 108 to pivot valve face 106a away from pressure plate 94 through a greater angle that would otherwise be possible, without closing off fluid flow through flexible tubing 34 due to compression of the flexible tubing by balance block 42. Inlet cracking valve pivot mounts 102 are connected to downwardly depending pivot arms 136 on inlet cracking valve 46, at each side of flexible tubing 34, and are centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, thereby increasing the force exerted by that part of inlet cracking valve 46 to compress the flexible tubing. The stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated for by balance block 42.

Inlet cracking valve 46 operates in three distinct modes, the force applied by valve face 106a to compress flexible tubing 34 being substantially different in each mode. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determines the three modes in which inlet cracking valve 42 operates. Inlet valve cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and to provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends is mounted to frame 100 in bearings 220 (see FIG. 5). A motor shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the closure flexure against the side arm and thereby reducing the total force exerted by valve face 106a against flexible tubing 34. In this configuration, inlet cracking valve 46 is in a "cracking mode."

As hood 126 moves further radially outward, closure flexure 120 contacts a "V-shaped" side arm 118 that is formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of plunger 48, and is thus disposed to roll along plunger cam track 152. Also mounted on base 156, at opposite sides of roller 154, are tubing shaper rollers 160. The disposition of tubing shaper rollers 160 is more clearly shown in FIG. 5, and their operation in respect to shaping flexible tubing 34 is disclosed in detail below.

As shown using hidden lines in FIG. 4, the back side of cam assembly 142 includes a torque compensation track 170. A conically-shaped or tapered torque compensation roller 172 rolls along torque compensation track 170, applying a rotational torque to cam assembly 142 that compensates for an opposite torque resulting from rapid changes in the shape of inlet valve cam track 140, outlet valve cam track 150, and plunger cam track 152. Torque compensation roller 172 is mounted on a flat metal spring torque compensation flexure 174 that applies a biasing force to the torque compensation roller, forcing it against torque compensation track 170 on cam assembly 142.

Like inlet cracking valve 46, outlet cracking valve 52 has a generally "Y-shaped" configuration and includes an outlet valve arm 180, which is connected to outlet valve face 106b and to balance block 58. On opposite sides of flexible tubing 34, pivot arms 136 extend downwardly, connecting to outlet cracking valve pivot mounts 104 on frame 100. Balance block 58 rests on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top of outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet valve cam track 150. The lower ends of follower flexure 196, cracking flexure 182, and closure flexure 188 are all secured at blocks 130 to bracket 135 by bolts 132, just as the corresponding elements are in respect to inlet cracking valve 46. As outlet valve cam follower 190 follows outlet valve cam track 150, hood 194 periodically contact closure flexure 188, lifting it away from side arm 186 so that the flow control force provided by cracking flexure 182, added to the balance force developed by balance blcok 58, is transmitted to valve face 106b, thereby compressing flexible tubing 34 against pressure plate 94 with a cracking force. In this configuration, outlet cracking valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

A strain gauge 198 is mounted to cracking flexure 182. Strain gauge 198 develops an output signal corresponding to the stress developed in cracking flexure 182, therefore indicating the pivotal motion of outlet valve arm 180 as it rotates to allow fluid flow past outlet cracking valve 52. Accordingly, strain gauge 198 comprises flow detector 54 for determining whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the pivotal motion of outlet valve arm 180, indicating that fluid flow past outlet cracking valve 52 has not occurred during a pumping stroke of plunger 48. Accordingly, the signal from strain gauge 198 can be used to detect whether container 32 has run dry or whether flow of liquid 31 into volumetric pump 30 has otherwise been interrupted. The signal produced by strain gauge 198 is simply a "go/no-go" signal as opposed to a signal that is accurately proportional to the movement of outlet valve arm 180. This go/no-go signal is used to stop volumetric pump 30 and initiate an alarm when the expected fluid flow is not obtained, thereby alerting medical personnel of the problem so that it can be corrected. It should be noted that the detection of an interruption fluid flow from volumetric pump 30 by flow detector 54 represents an entirely different alarm condition than the detection of an occlusion. It is possible that a partial occlusion of the proximal or distal portions 34a, 34c of the flexible tubing might allow sufficient fluid to flow from volumetric pump 30 so that a flow interruption is not detected. However, the occlusion should be detected by the occlusion detection system incorporated into volumetric pump 30 to insure that a patient receives the correct dosage of medication during a prescribed interval of time.

Instead of strain gauge 198, various other types of motion sensors may be used to produce a signal indicative of the pivotal motion of outlet valve arm 180. For example, outlet valve arm 180 can be connected to a linear variable displacement transformer (LVDT) that uses motion to produce a signal corresponding to a relative change in the magnetic coupling between two electromagnetic coils, or may comprise a variable capacitor that changes capacitance value as outlet valve arm 180 pivots. Similarly, a Hall sensor or optical sensor can be used to detect pivotal motion of outlet valve arm 180, and thus may serve as alternative types of flow detectors.

In FIG. 5, details of tubing shapers 50a and 50b are disclosed. Since it is preferable to use relatively low cost PVC tubing in connection with volumetric pump 30, tubing shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal, round, uncompressed shape from a compressed condition rapidly enough to fill completely with fluid. Accordingly, the volumetric displacement of fluid within the PVC tubing that occurs with each pumping stroke is less than desired. To avoid this problem, tubing shapers 50a and 50b force pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tubing shaper 50a and 50b comprises an angled arm 234, terminating at one end in a longitudinally-extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tubing shaper rollers 160 in "lock-step", causing jaws 236 to pinch pumping portion 34b of the flexible tubing at the proper time, thereby reforming flexible tubing 34 into the required pumping volume or capacity as plunger 48 lifts away from pressure plate 94. In FIG. 5, tubing shapers 50a and 50b are shown moving in oppsite directions, away from pumping portion 34b of the flexible tubing as plunger 48 descends to compress flexible tubing 34, displacing fluid from pumping portion 34b. To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lower-most point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

OCCLUSION DETECTION SYSTEM

Figure 7:
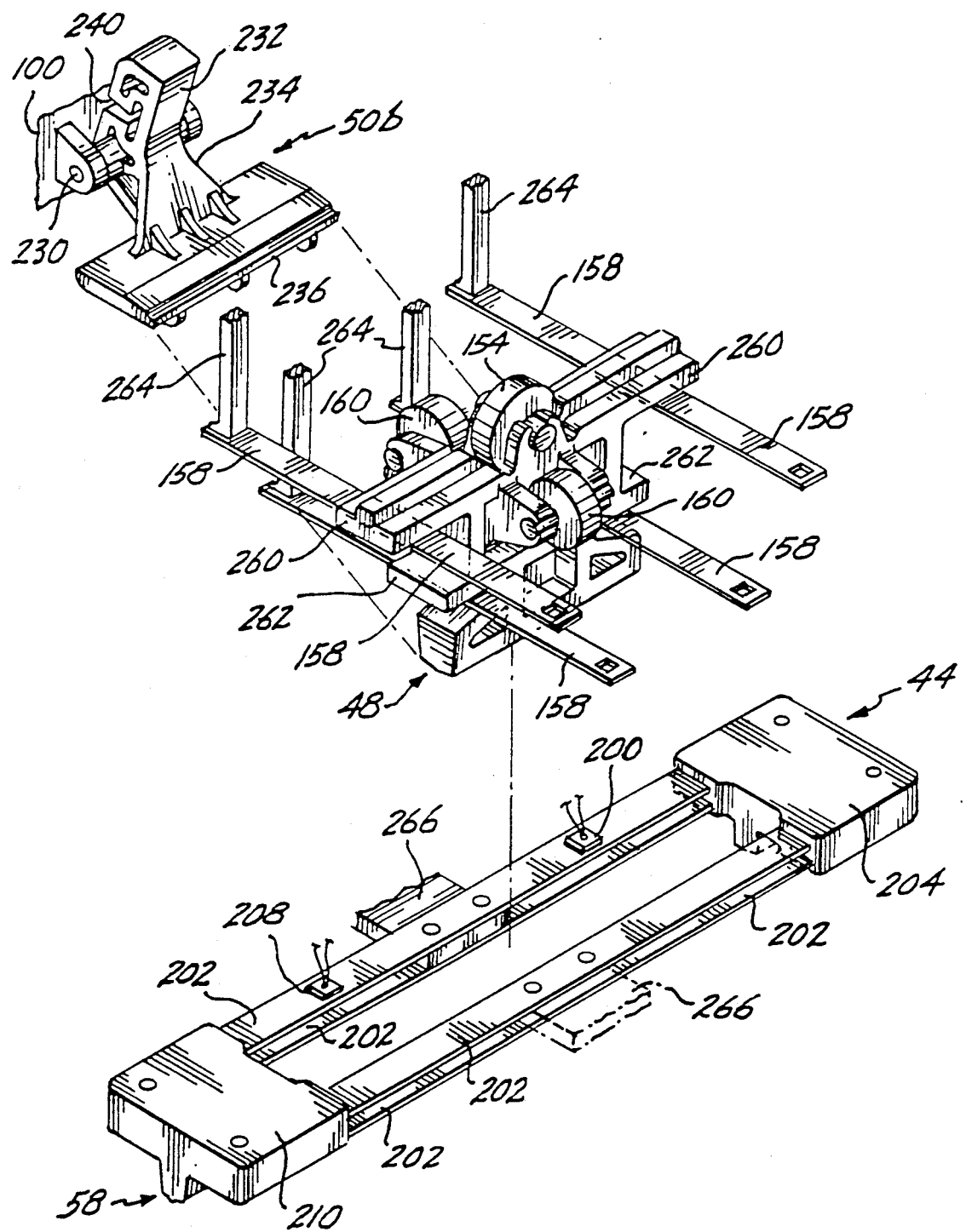
FIG. 7 is an exploded view of a portion of the pump assembly, showing the plunger suspension assembly and details of the strain gauges used for sensing proximal and distal pressure.

With reference to FIGS. 4 and 7, proximal pressure sensor 44 comprises a block 204, which is spring biased into contact with proximal portion 34a of the flexible tubing, and is disposed between inlet cracking valve 46 and balance block 42. A spring-bias force for proximal pressure sensor 44 is provided by two pairs of longitudinally-extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, the cross-sectional size of the flexible tubing increases (i.e., the diameter expands) so that flexures 202, which are connected to block 204, experience increased stress, producing a corresponding change in the output signal from strain gauge 200 that is proportional to the fluid pressure within the proximal portion 34a.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produces a signal corresponding to the fluid pressure within distal portion 34c of the flexible tubing, based upon stress developed in flexures 202 as a result of that pressure changing the cross-sectional size (i.e., diameter) of distal portion 34c of the flexible tubing. Distal pressure sensor 56 is used to determine, for example, if distal portion 34c of the flexible tubing has been kinked or pinched, reducing fluid flow through flexible tubing 34, as might occur if a patient rolled over onto the flexible tubing. Such a condition causes a notable increase in the distal fluid pressure that triggers an occlusion alarm and shuts off volumetric pump 30. In response, an operator can quickly correct the condition interrupting fluid flow through the distal portion and restart the volumetric pump, since the nature and general area of the occlusion are identified by the alarm condition data displayed to the operator on display 76 (shown in FIG. 2).

Figure 8:
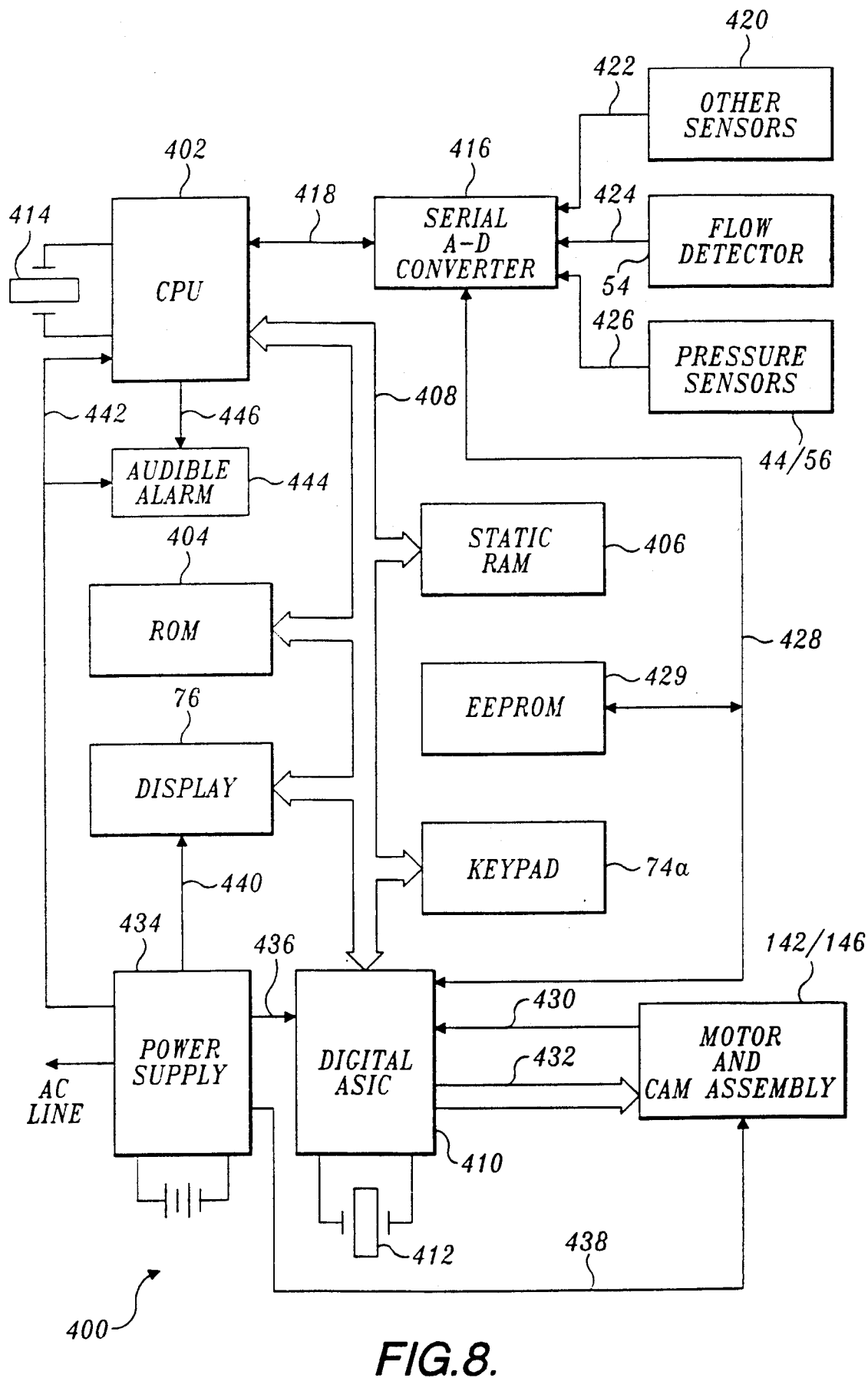
FIG. 8 is a schematic block diagram showing a control for the pump.

FIG. 8 schematically illustrates a control 300, which is electronically connected to control panel 74 to respond to operator selection of input data provided thereby and to display data and alarm conditions to the operator on display 76, in addition to controlling the operation of volumetric pump 30. In respect to the present invention, control 300 responds to the signals produced by strain gauges 200 and 208 in monitoring the proximal and distal pressures, which are used in detecting an occlusion of the proximal portion 34a or the distal portion 34c of the flexible tubing. Control 300 includes a central processing unit 302, a nonvolatile read-only memory (ROM) circuit 304 in which are stored program instructions for controlling volumetric pump 30, and a static random-access memory (RAM) circuit 306 in which data developed during the operation of the pump are temporarily stored. ROM circuit 304 also stores the program code that controls detection of an occlusion of either proximal or distal portions 34a and 34c of the flexible tubing in response to the pressures within the proximal and distal portions. ROM circuit 304 and RAM circuit 306 are electronically connected to CPU 302 by a combined bidirectional, eight-bit-wide, address/data/control bus 308. In the preferred form of the invention, CPU 302 comprises an 8 MHz, NEC Type V25 microcomputer circuit, having a 16 MHz crystal 314 to provide a timebase. Bus 308 is also connected to convey control signals, data, and address information to display 76 and to a digital application-specific integrated circuit (ASIC) 310. A 3.2 MHz crystal 312 provides a timebase for ASIC 310.

ASIC 310 is not required for occlusion detection; the primary advantage of ASIC 310 in volumetric pump 30 relates to its use in the control of motor 146, which drives cam assembly 142—not in the detection of occlusions. Accordingly, a description of the design details of the ASIC is not required for an enabling disclosure of the occlusion detection functions implemented by control 300.

An eight-channel, eight-bit, serial analog-to-digital (A-D) convertor 316 converts the analog signals from a plurality of sensors to digital signals that can be used by CPU 302. For example, other sensors 320, which are not related to the present invention, supply analog signals to A-D convertor 316 over signal leads 322. Of greater relevance to the detection of occlusion, proximal pressure sensor 44 and distal pressure sensor 56 respectively supply analog signals indicative of fluid pressure within the proximal and distal portions of the flexible tubing to A-D convertor 316 over signal leads 324 and 326. As explained above, these analog signals are produced by strain gauges 200 and 208, respectively. The analog signals are amplified by conventional amplifiers (not separately shown) before being supplied to A-D convertor 316. A-D convertor 316 converts these analog signals to corresponding digital signals under the control of CPU 302; the CPU supplies control signals to the A-D convertor over a control lead 318. A lead 328 carries serial clock, serial data-in, and serial data-out signals between ASIC 310 and A-D convertor 316. The digital signals corresponding to the fluid pressures in the proximal and distal portions of the flexible tube 34 are supplied in serial format to ASIC 310 over lead 328. ASIC 310 converts the serial signals to parallel format for use by CPU 302. Alternatively, a parallel A-D convertor could be used instead of A-D convertor 316, thereby eliminating the need for ASIC 310 to convert the format of the signals. The steps carried out by CPU 302 in determining whether an occlusion of the proximal or distal portions 34a, 34c has occurred are based upon the digital signals corresponding to the proximal and distal pressures, as described below.

As noted above, the principal advantage of ASIC 310 in volumetric pump 30 is in controlling motor 146. ASIC 310 is connected to supply control signals to motor 146 over leads 332. A lead 330 conveys motor and cam assembly position signals back to ASIC to provide feedback indicating the rotational position of cam assembly 142, which is important in determining when proximal and distal pressure signals are monitored during the pumping cycle of volumetric pump 30.

Control 300 also includes a combination battery/AC line energized power supply 334. Appropriate DC power supply voltages are provided to each of the components of control 300 that require electrical power by power supply 334 over several power leads, including a lead 336, which conveys power to ASIC 310. Similarly, leads 338, 340, and 342 carry power to motor 146, display 76, and CPU 302, respectively. Lead 342 also conveys power to an audible alarm 344, which is controlled by CPU 302 in response to signals provided over a lead 346. Audible alarm 344 is used to alert an operator of volumetric pump 30 when an occlusion or some other operating fault has occurred that requires corrective action by the operator.

Figure 9:
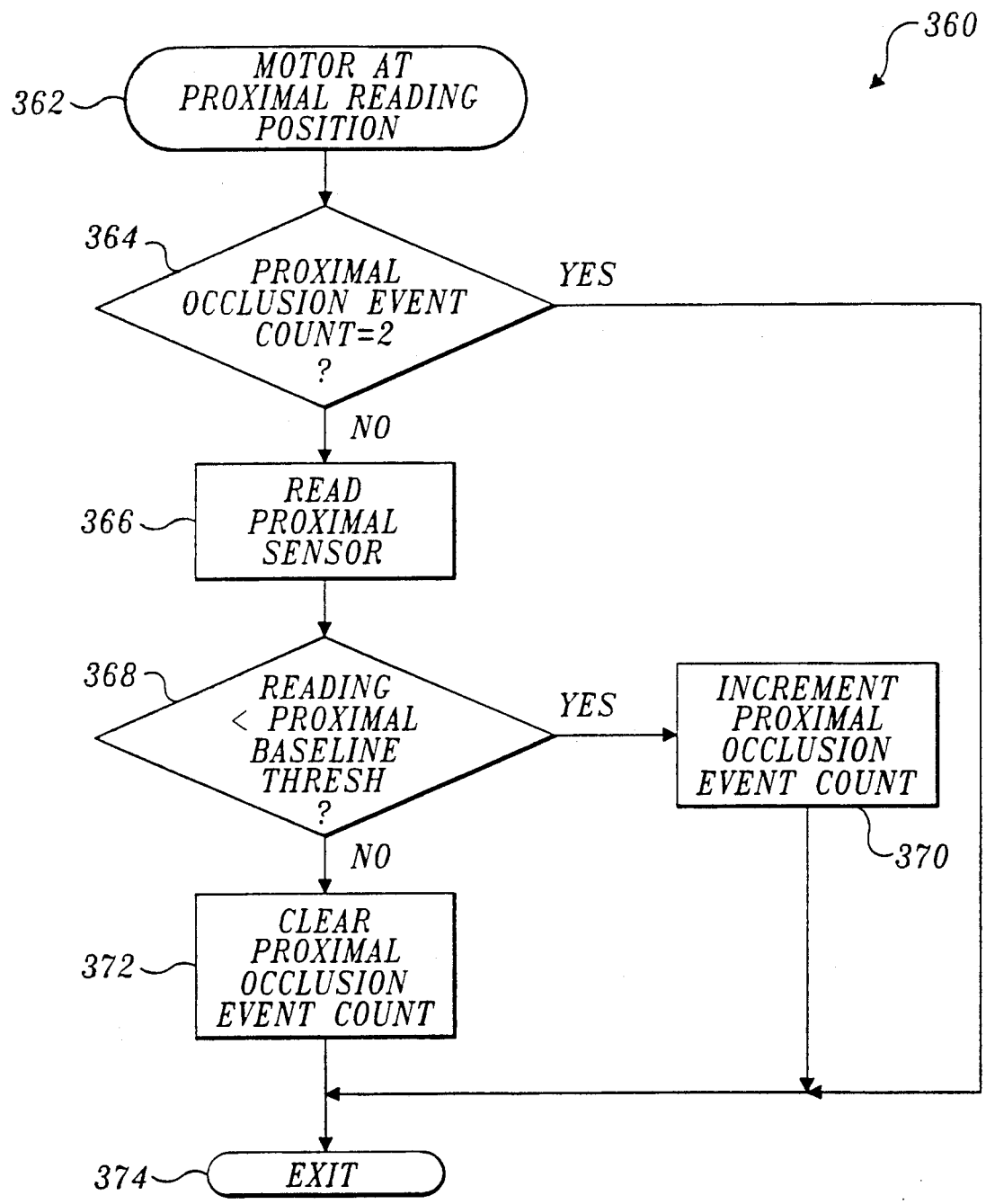
FIG. 9 is a flow chart showing the logic steps used in detecting preconditions for a proximal occlusion.

Turning now to FIG. 9, a flow chart showing the steps implemented by CPU 302 in detecting preconditions for a proximal occlusion is shown and starts at a block 362, when motor 146 is at a proximal reading position. The proximal reading position corresponds to revolution 8 in the 24 revolutions of motor 146 that comprise a single pumping cycle. As noted above, feedback signals indicative of the number of revolutions of motor 146 and of the home position of cam assembly 142 are developed within volumetric pump 30. CPU 302 is thus provided with data indicating the relative progress of volumetric pump 30 through each of its pumping cycles. Revolution 0 of the motor begins at the coincidence of the home positions of motor 146 and of cam assembly 142, and ends one MOTOR_HOME pulse later, at the beginning of motor revolution 1. Accordingly, as indicated in box 362, proximal readings are taken at each motor revolution 8, after allowing an initial conditioning time, as indicated by a variable, PRESSURE_ENABLE.

In a decision block 364, a determination is made as to whether a proximal occlusion event count is equal to two. The proximal occlusion event count is incremented each time that the proximal pressure signal is less than a proximal baseline threshold, as will be evident from the following steps. Assuming that the event count is equal to two, the logic continues to an exit block 374. However, if the proximal occlusion event count is less than two, the logic proceeds to a block 366 wherein the proximal sensor signal is read, i.e., converted to a digital value as explained above, for input to CPU 302. If the proximal pressure sensor reading is less than the proximal baseline threshold, a decision block 368 routes the flow of logic to a block 370, in which the proximal occlusion event count is incremented by one. The logic then again proceeds to exit block 374. Alternatively, if the proximal pressure signal exceeds the proximal baseline threshold, a block 372 provides for clearing the proximal occlusion event count. At least three consecutive proximal pressure readings must fall below the current proximal pressure baseline to trigger a proximal occlusion alarm. Therefore, block 372 clears the event counter whenever a proximal pressure reading is above the proximal pressure baseline.

Figure 10:
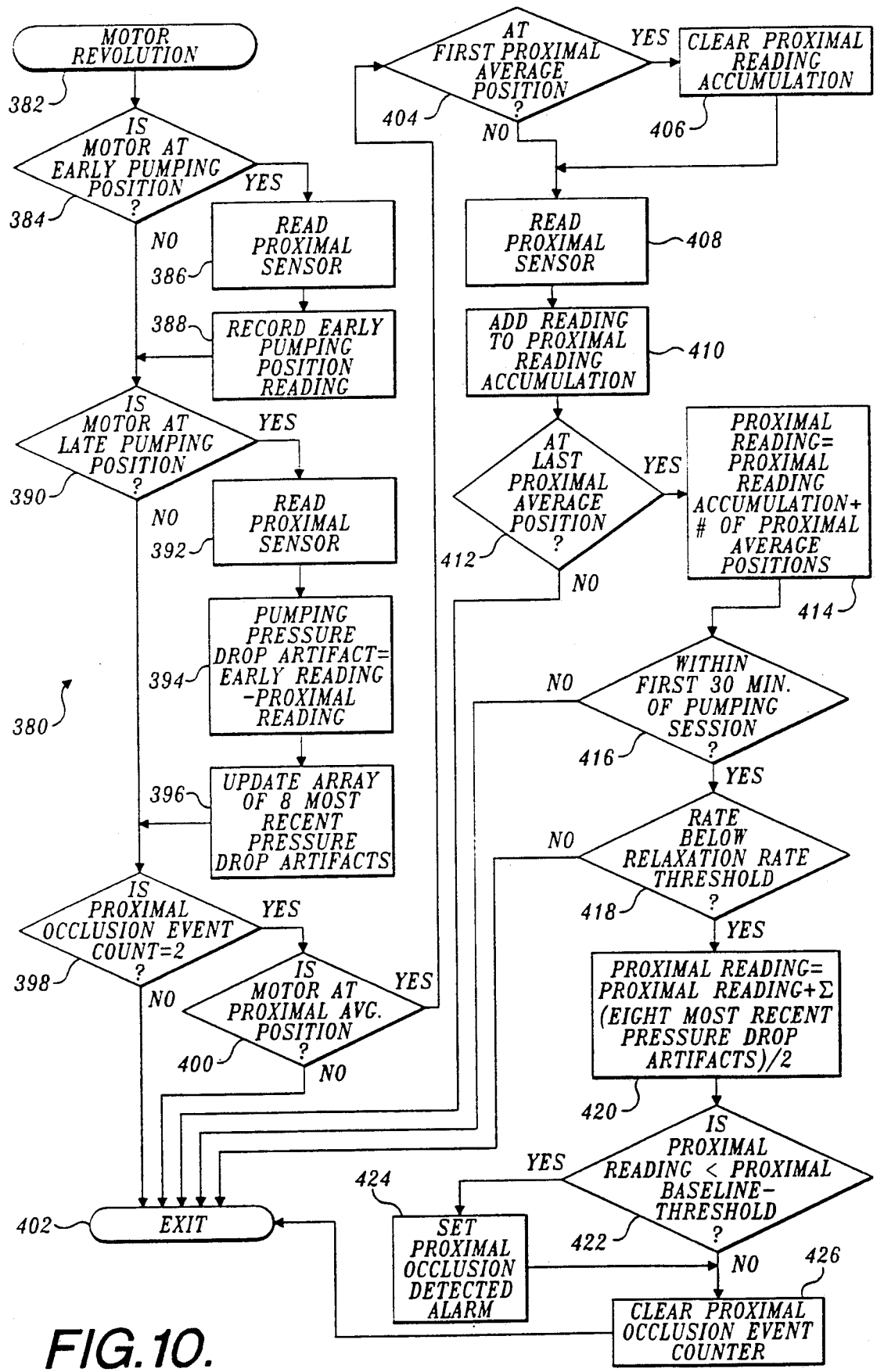
FIG. 10 is a flow chart showing the steps used to reject artifacts (noise) in monitoring for a proximal occlusion.

Several factors can contribute to "noise" that affects the proximal pressure, causing it to sporadically drop below the proximal pressure baseline. Accordingly, it is necessary to remove such artifacts or compensate for their presence, to ensure that a proximal occlusion is correctly detected. FIG. 10 is a flow chart that includes steps for rejecting such artifacts. Variations in the proximal pressure signal that comprise unwanted artifacts include mechanical, electrical, and thermal noise, and changes in the proximal pressure reading due to relaxation of flexible tubing 34 over time, after it is initially installed. To compensate for changes in the signal to tubing relaxation, the algorithm keeps track of the progression of both time and the pumping cycle. A block 382 provides for determining the specific revolution of motor 146 (of the 24 revolutions comprising one pumping cycle). A decision block 384 determines if the motor is at an early pumping position, corresponding to revolution 3 during each pumping cycle. If the motor is at this position, in a block 386, the signal produced by the proximal pressure sensor is read, and its digital value is recorded within CPU 302, as provided at a block 388. However, if the motor is not at the early pumping position, or following block 388, a decision block 390 determines if the motor is at its late pumping position, corresponding to revolution 8. Assuming that the motor is at revolution 8, a block 392 provides for reading the proximal pressure sensor.

In block 394, a pumping pressure drop artifact is determined; this value is equal to the difference between the proximal pressure reading at revolution 3 and at revolution 8 of motor 146. An array of the eight most recent pressure drop artifacts is maintained by CPU 302, and in block 396, the array is updated so that the most recent reading is included in the array. Referring back to decision block 390, if the motor was not at its late pumping position (revolution 8), or, following the update in block 396, a decision block 398 determines if the proximal occlusion event count is equal to two. Assuming that it is, a block 400 determines if the motor is at a proximal averaging position. A proximal averaging position comprises motor revolutions 0, 2, 4, 6, and 8. If the results of either decision block 398 or decision block 400 are negative, the logic proceeds to an exit block 402.

However, if the motor is at one of the proximal averaging positions, a decision block 404 determines if it is at the first averaging position (revolution 0). If so, a block 406 clears the proximal reading accumulation to initiate a new accumulated reading. If the result of decision block 404 is negative, or, following block 406, a block 408 causes CPU 302 to read the proximal pressure sensor signal, and in block 410, the reading is added to the previous accumulated reading for that pumping cycle.

A decision block 412 then determines if the motor is at its last proximal averaging position (revolution 8), and if so, a block 414 sets the proximal reading equal to the proximal reading accumulation divided by the total number of proximal averaging positions (five). It should be apparent that block 414 thus determines an average proximal reading for the proximal pressure readings taken at each of revolutions 0, 2, 4, 6, and 8. Thereafter, decision block 416 determines if the motor has been operating for less than 30 minutes, such that relaxation of flexible tubing 34 should have stabilized. If the response is affirmative, a decision block 418 determines if the pumping rate is below a relaxation rate threshold.

In the preferred embodiment, the relaxation rate threshold is 60 milliliters per hour. In other words, decision block 418 determines whether the operator has set volumetric pump 30 to produce a fluid flow rate of less than 60 milliliters per hour. If the response to decision block 418 is affirmative, a block 420 sets the proximal reading equal to the last proximal reading plus the sum of the eight most recent pressure drop artifacts (contained in the array referenced in block 396) divided by two. The correction provided in block 420 compensates for the relatively long period required for pumping cycles at rates less than 60 milliliters per hour and the effect of flexible tubing relaxation upon the determination of a proximal occlusion.

A decision block 422 then determines if the proximal reading is less than the difference between the proximal baseline and the threshold. A block 424 sets the proximal occlusion detected alarm to warn an operator both visually and audibly that a proximal occlusion has occurred if the results of decision block 422 are affirmative. It should be noted that the alarm can only occur if the proximal occlusion event count has already reached two, as a result of branching from decision block 398. However, if the proximal reading exceeds the difference between the proximal baseline and the threshold (6 psig in the preferred embodiment), a block 426 clears the proximal occlusion event counter and then proceeds to exit block 402. Similarly, negative responses to decision blocks 400, 412, 416, and 418 also lead to exit block 402.

Figure 11:
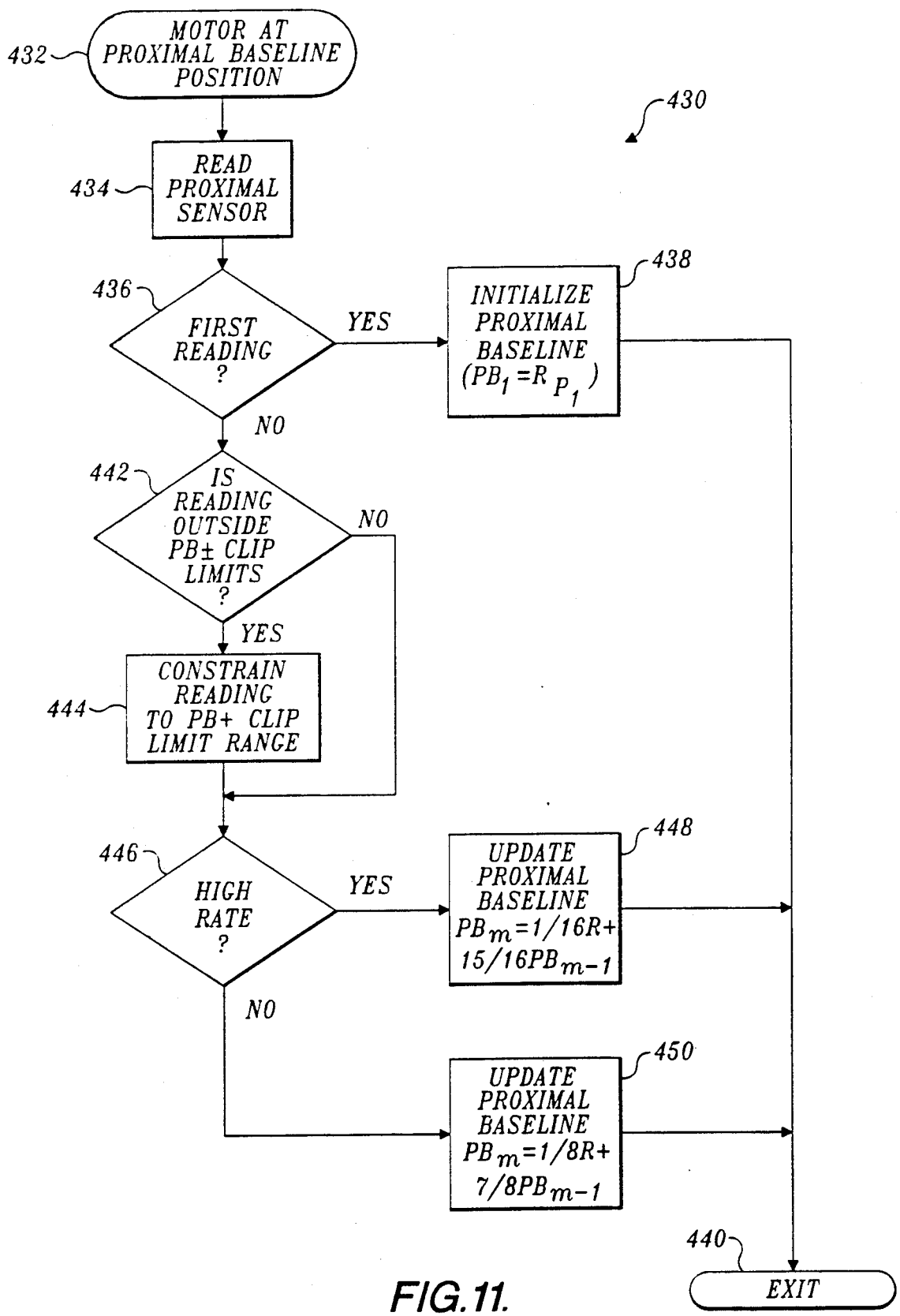
FIG. 11 is a flow chart illustrating the logic steps used to determine and maintain a proximal pressure baseline.

In FIG. 11, a flow chart 430 illustrates the steps necessary to determine the proximal pressure baseline, starting at a block 432 that is initiated when the motor is at the proximal baseline position (revolution 8). At this time, a block 434 provides for reading the proximal pressure sensor, and in decision block 436, if the reading represents the first revolution in the pumping cycle, a block 438 initializes the proximal baseline with a first value equal to that proximal pressure reading. Thereafter, the flow of logic proceeds to an exit block 440.

Alternatively, if the reading in block 434 is not the first reading in the pumping cycle, a decision block 442 determines whether this reading is outside the proximal pressure baseline clip limits (+/−10 psig relative to the current baseline pressure). If outside the clip limits, block 444 constrains the proximal pressure reading to the proximal pressure baseline plus the clip limit range, i.e., limits the proximal pressure reading to the previous baseline value ±10 psig. If the reading is not outside the clip limits, the logic flows around block 444.

In a decision block 446, CPU 302 determines whether the volumetric pump is operating at a high rate (i.e., at a nominal pumping flow rate greater than or equal to 125 milliliters per hour), and if so, a block 448 updates the proximal pressure baseline, setting it equal to 1/16 of the current proximal pressure reading plus 15/16 of the previous proximal pressure baseline. Thereafter, the program proceeds to exit block 440. However, if the volumetric pump is not operating at the nominal high rate of flow, a block 450 sets the proximal pressure baseline equal to ⅛ of the current proximal pressure reading plus ⅞ of the previous proximal pressure baseline, before proceeding to exit block 440.

The steps implemented in blocks 448 and 450 of flow chart 430 thus provide a weighted average for the proximal pressure baseline, which is used in determining whether a proximal occlusion has occurred. Further, this weighted average accommodates different fluid pumping rates and is weighted to compensate for flexible tubing relaxation, which occurs most rapidly when the flexible tubing is first put into use within volumetric pump 30.

Figure 12:
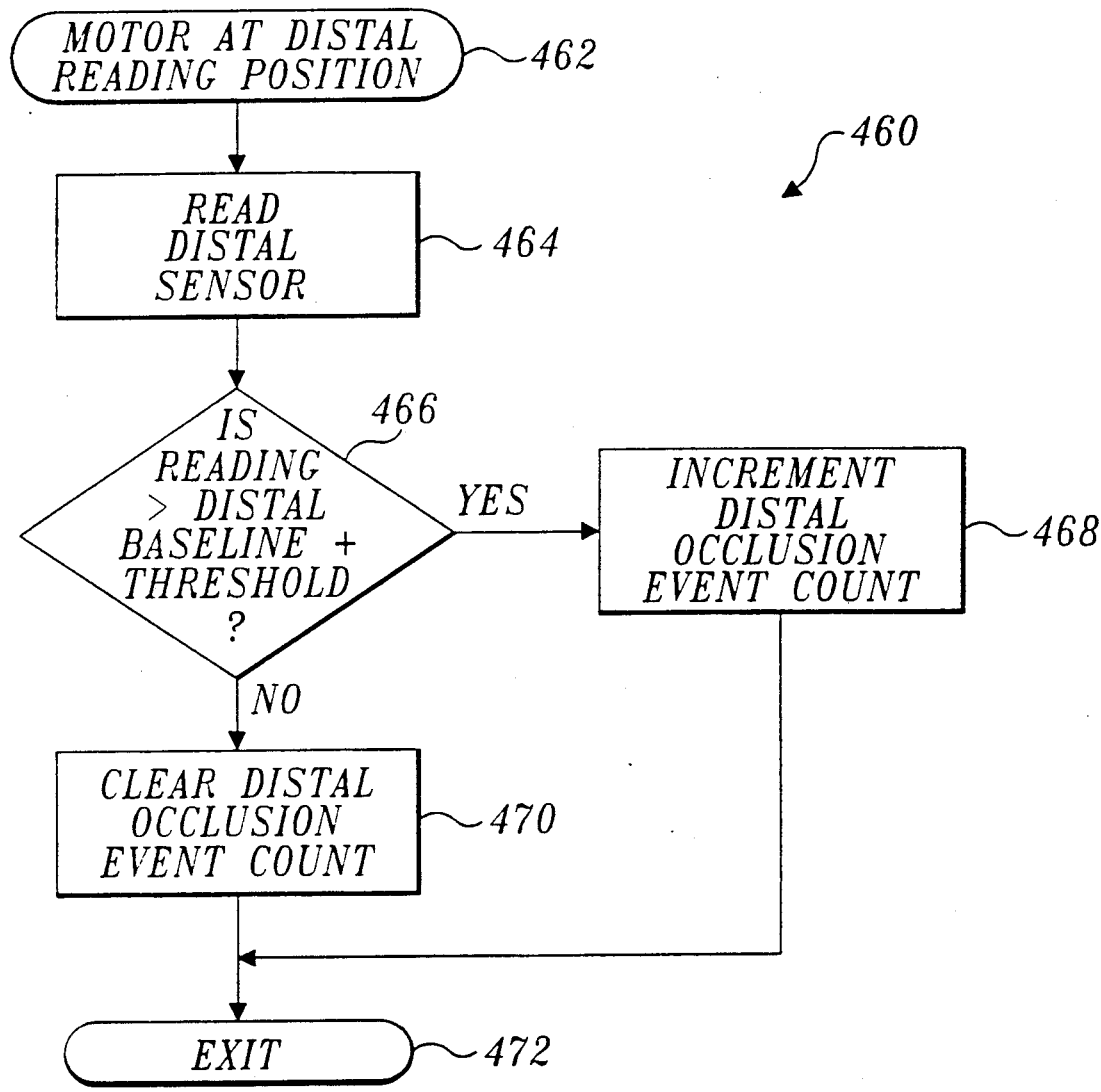
FIG. 12 is a flow chart illustrating the steps employed for detecting preconditions for a relative distal occlusion.

In FIG. 12, a flow chart 460 illustrates the steps required for detecting preconditions for a relative distal occlusion, starting when motor 146 is at a distal reading position (revolution 22), as provided in a block 462. At that time, a block 464 instructs CPU 302 to read the distal pressure sensor signal in digital format, and a decision block 466 determines if the reading is greater than the distal pressure baseline plus a threshold. Determination of the distal pressure baseline is described below.

In the preferred embodiment, the threshold is user-selected at either 6 psig (Lo), or 12 psig (Hi). Just as was the case for proximal occlusion detection, three consecutive distal pressure readings must indicate an occlusion in order to initiate a distal occlusion alarm. Therefore, if the reading in decision block 466 exceeds the sum of the distal pressure baseline and the threshold, a block 468 increments the distal occlusion event counter maintained by CPU 302. The flow of logic then procees to an exit block 472. However, if the response to decision block 466 is negative, a block 470 clears the distal occlusion event counter before proceeding to exit block 472.

Figure 13:
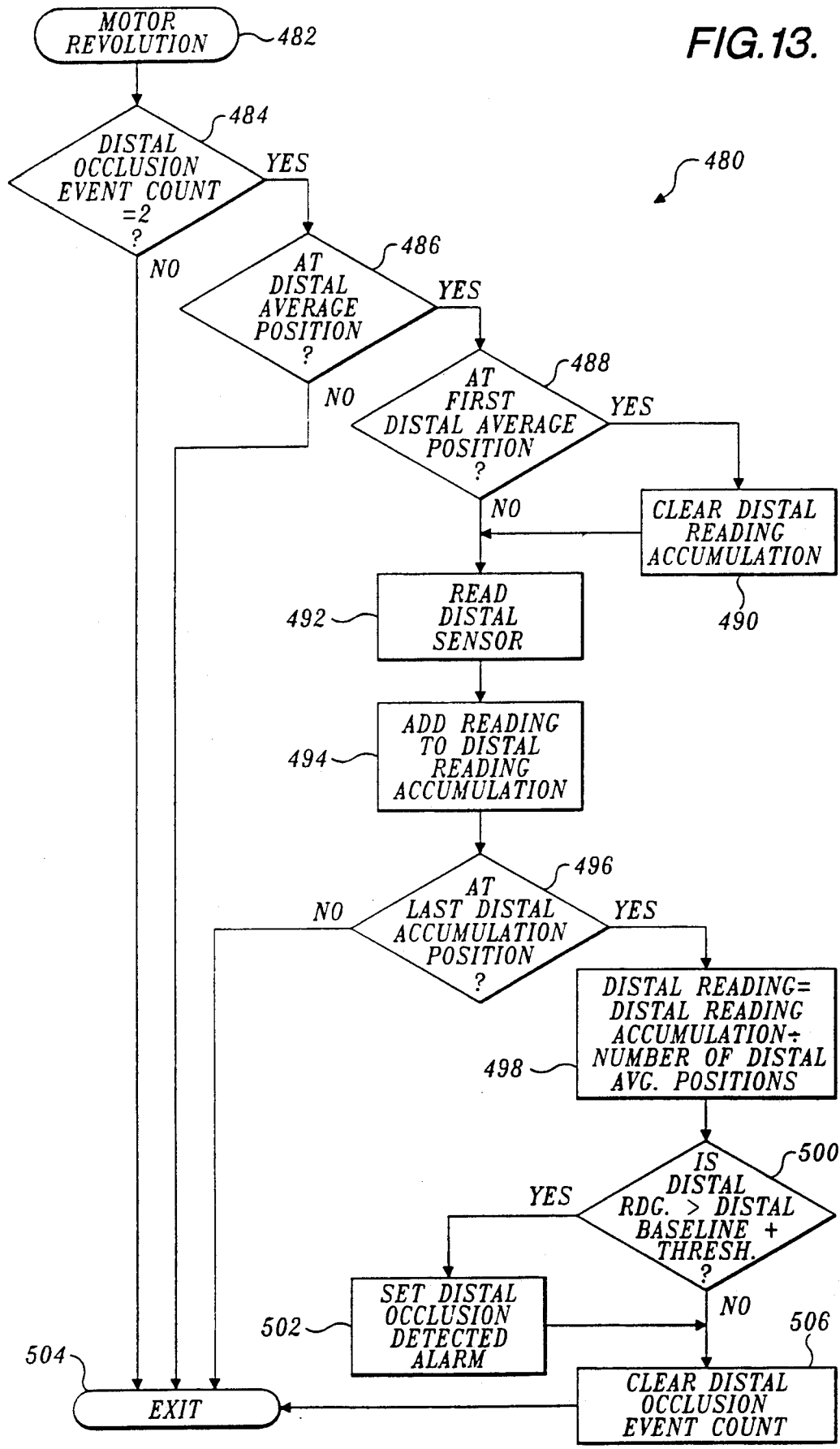
FIG. 13 is a flow chart showing the logic steps used to reject distal reading artifacts.
Figure 14:
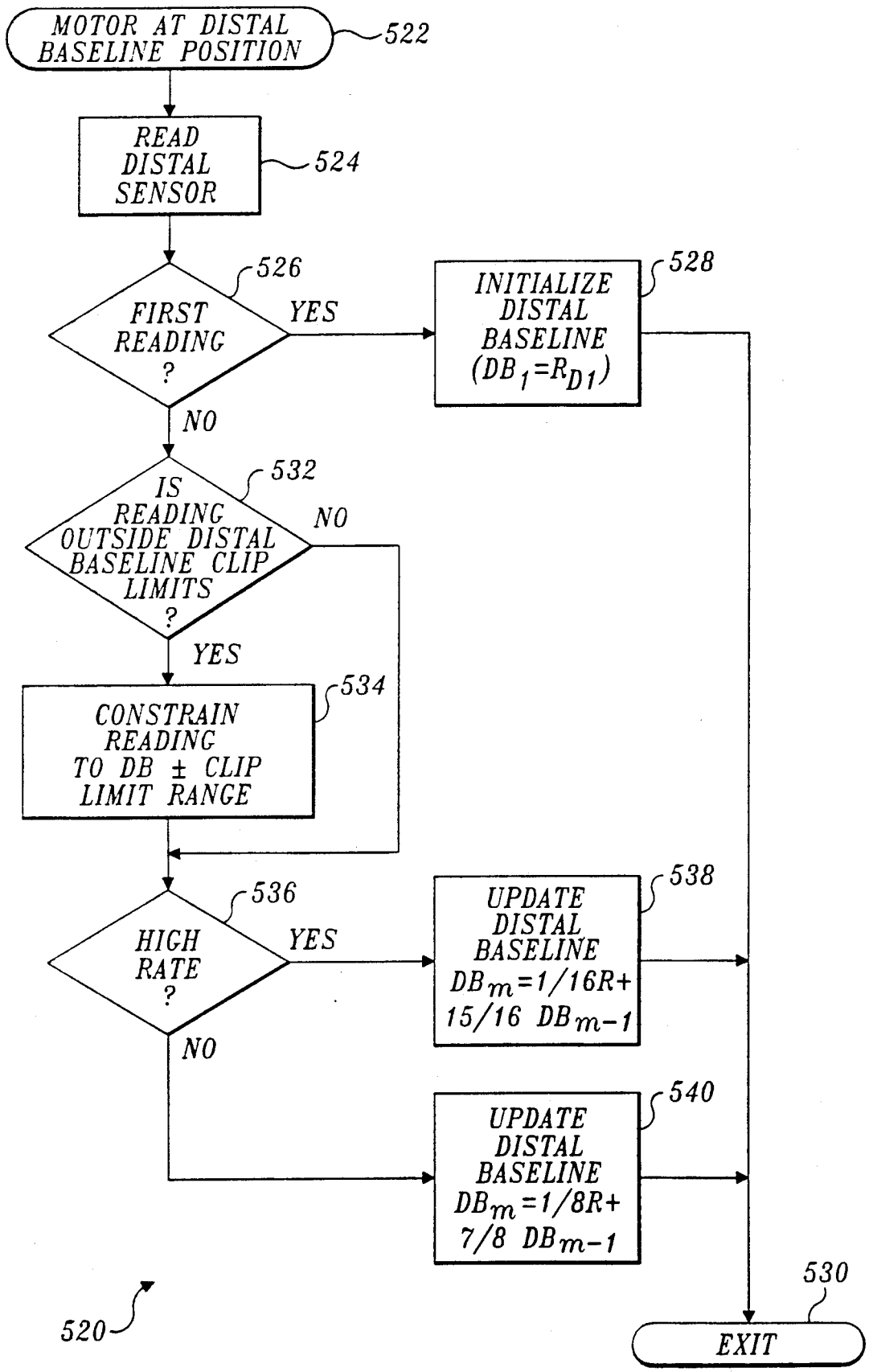
FIG. 14 is a flow chart showing the logic steps for determining and maintaining the distal pressure baseline.

The same types of noise and other artifacts noted with respect to proximal pressure signals are also evident in the distal pressure signal. Accordingly, in FIG. 13, a flow chart 480 discloses the steps used to reject artifacts that would otherwise cause errors in the detection of distal occlusions. A block 482 responds to each motor pulse, causing the logic to proceed to a decision block 484, which determines if the distal occlusion event counter is equal to two. If not, the flow of logic proceeds to an exit block 504. However, after two occlusion events have been detected in succession, an affirmative response to decision block 484 leads to a decision block 486, which determines whether the motor is at one of the distal averaging positions, corresponding to revolutions 12, 14, 16, 18, and 20. An affirmative response leads to a decision block 488, which determines if the motor is at the first distal averaging position (revolution 12) and, if so, the previous distal reading accumulation is cleared in a block 490. Thereafter, or, in response to a negative determination in decision block 488, CPU 302 reads the distal pressure sensor at a block 492. In a block 494, the current distal pressure readings are added to the previous distal pressure readings accumulated by the CPU.

A decision block 496 then determines if the motor is at its last distal pressure accumulation position (revolution 20) and, if so, sets the distal pressure reading equal to the total distal pressure reading accumulation divided by the number of distal averaging positions (five). The resulting averaged distal pressure reading is then compared to the sum of the distal pressure baseline and threshold in a decision block 500. If the average distal pressure reading is greater than the sum of the distal pressure baseline and threshold, a block 502 sets the distal occlusion detected alarm, causing both a visual and audible alarm to alert the operator that a distal occlusion has occurred. Thereafter, or following a negative response to decision block 500, a block 506 clears the distal occlusion event counter and proceeds to exit block 504. Negative responses to decision blocks 486 and 496 also result in logic flow proceeding to exit block 504.

A flow chart 520 sets forth the steps for determining the distal pressure baseline, starting at a block 522 that initiates the distal pressure sensor reading when the motor is at revolution 22. CPU 302 thus reads the distal pressure sensor in a block 524 at that time, and in a decision block 526 determines if the reading is the first in the pumping session. If so, a block 528 initializes the distal pressure baseline, setting it equal to that first reading. Thereafter, the logic flow exits at an exit block 530.

If not the first pressure reading, a decision block 532 determines whether the reading is outside the distal baseline pressure clip limits ($+/-10$ psig). If so, in a block 534, the readings are constrained to the distal baseline plus or minus the clip limit range. Thereafter, or if the reading was not outside the limits, a decision block 536 determines whether the volumetric pump is operating at a high flow rate (greater than or equal to 125 milliliters per hour), and, if so, proceeds to a block 538. Block 538 sets the distal baseline pressure equal to 1/16 of the present reading plus 15/16 of the previous distal pressure baseline. Thereafter, the logic flows to exit block 530. If the volumetric pump is not operating at a fluid flow rate in excess of the predefined high flow rate, a block 540 sets the distal pressure baseline equal to ⅛ of the current distal pressure reading plus ⅞ of the previous distal pressure baseline. The logic then proceeds to exit block 530.

Figure 15:
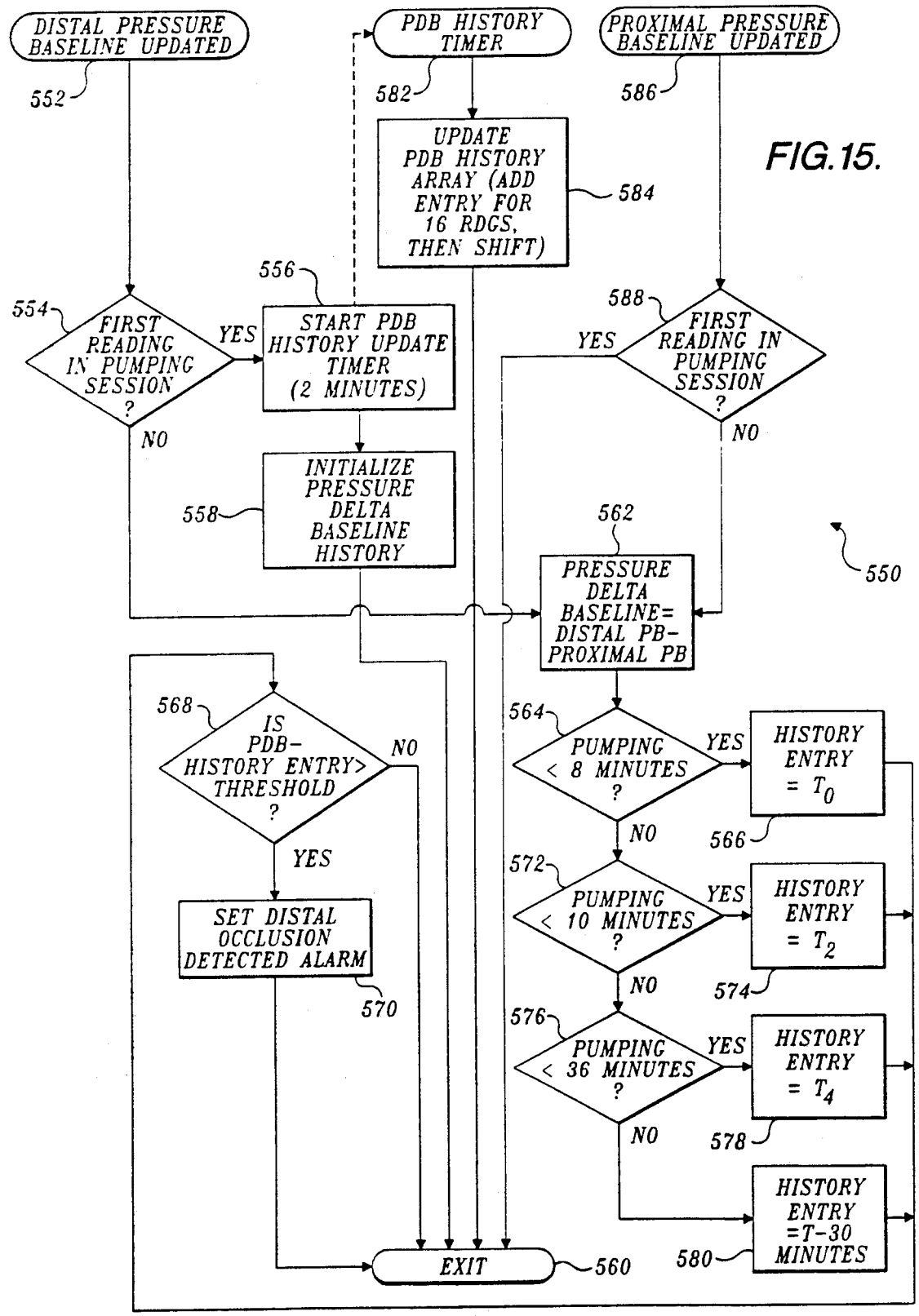
FIG. 15 is a flow chart showing the logic steps utilized for supplementary distal occlusion detection.

Distal occlusions are also detected on an absolute basis, according to the steps set forth in a flow chart 550, which is shown in FIG. 15. After the distal pressure baseline is updated in a block 552 (as described above), a decision block 554 determines whether a current reading is the first in the pumping session, and if so, a block 556 starts a pressure delta baseline (PDB) history update timer that runs for two-minute intervals. Block 556 is connected to control the PDB history timer, as provided in a block 582 and is connected to block 582 by a dashed line, as shown in FIG. 15. The PDB history timer controls the time at which the update of a PDB history array occurs, during which an additional entry is added to the array. There are no more than 16 readings in the array at any one time. Following block 584, the logic proceeds to an exit block 560. After block 556, a block 558 initializes a pressure delta baseline history, and then proceeds to exit block 560.

Following a negative response to decision block 554, a block 562 sets the pressure delta baseline equal to the distal pressure baseline minus the proximal pressure baseline. In order for block 562 to carry out this function, it must be provided with the proximal pressure baseline. A block 586 represents the input of the proximal pressure baseline data each time it is updated. From block 586, a decision block 588 determines if the proximal pressure baseline was developed solely from a first reading in the pumping session and, if so, proceeds to exit block 560. Otherwise, the proximal pressure baseline value is applied to block 562 from decision block 588.

Once the pressure delta baseline is determined in block 562, a decision block 564 determines if the pumping session has been underway for less than eight minutes. If the answer is affirmative, the entry to the PDB history array used for a subsequent comparison is set to the initial value in the array, which was determined at time $T_0$. If the pumping session has been in progress for at least eight minutes, a decision block 572 determines if the pumping session has continued for less than 10 minutes and, if so, uses a history entry that is equal to $T_2$, which represents the PDB history entry at the two-minute interval. Further, if the pumping session has extended for at least 10 minutes, but less than 36 minutes, a PDB history entry equal to T₄ (at the four-minute interval) is used for the subsequent comparison. Finally, if the pumping session has extended for 36 minutes or longer, the history entry used for the comparison is the one that occurred at a time equal to the actual duration of the pumping cycle minus 30 minutes. As the pumping session continues, the previous values stored in the array that are no longer required for the comparison are discarded.

In a decision block 568, the particular history entry selected in blocks 566, 574, 578, or 580 is compared to a predefined threshold. In the preferred embodiment, the threshold is equal to 14 psig. If the PDB history entry used in the comparison exceeds the threshold, a box 570 provides for setting a distal occlusion detected alarm that gives both a visual and audible warning to the user in a box 570. Thereafter, of if the response to decision block 568 is in the negative, the logic flow proceeds to exit block 560.

Figure 16:
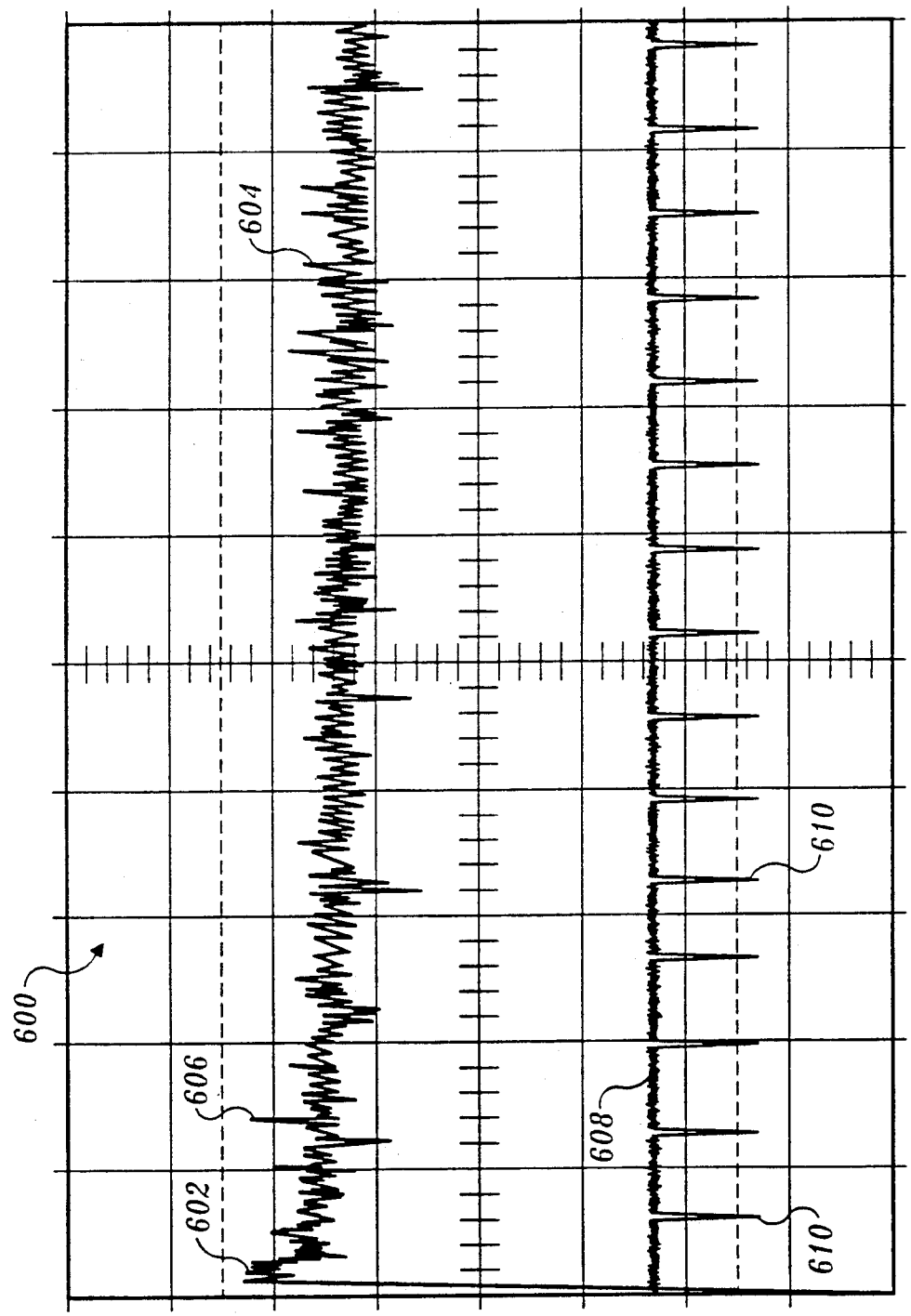
FIG. 16 graphically shows oscilloscope traces, including a trace of an output signal from the proximal pressure sensor during the first 15 minutes after a new tube set is installed in the volumetric pump, and a trace of the pulses produced each time the cam assembly in the volumetric pump passes its "home" position.

FIG. 16 illustrates an oscilloscope trace 600 of the proximal pressure sensor output signal during the first 15 minutes of a pumping session after a new flexible tubing 34 is installed. Volumetric pump 30 is set to provide a nominal 6 milliliters per hour of fluid flow. Also shown is an oscilloscope trace 608 of the signal produced by the reed switch used to detect rotation of cam assembly 142 past its home position. With reference to trace 600, it should be apparent that an initial portion 602 of the trace has a relatively higher average amplitude than a subsequent portion 604. The change in average amplitude results from the relaxation of flexible tubing 34 from when it is first installed within volumetric pump 30. Also shown are noise peaks, such as peak 606, which represent electrical and thermal noise artifacts that must be averaged out of the signal to provide an accurate clear indication of proximal occlusion.

As shown at the bottom of FIG. 16, trace 608 includes a plurality of pulses 610, each indicating completion of a pumping cycle as cam assembly 142 rotates past its home position. Each rotation of the cam assembly requires approximately one minute at the selected delivery rate.

Figure 17:
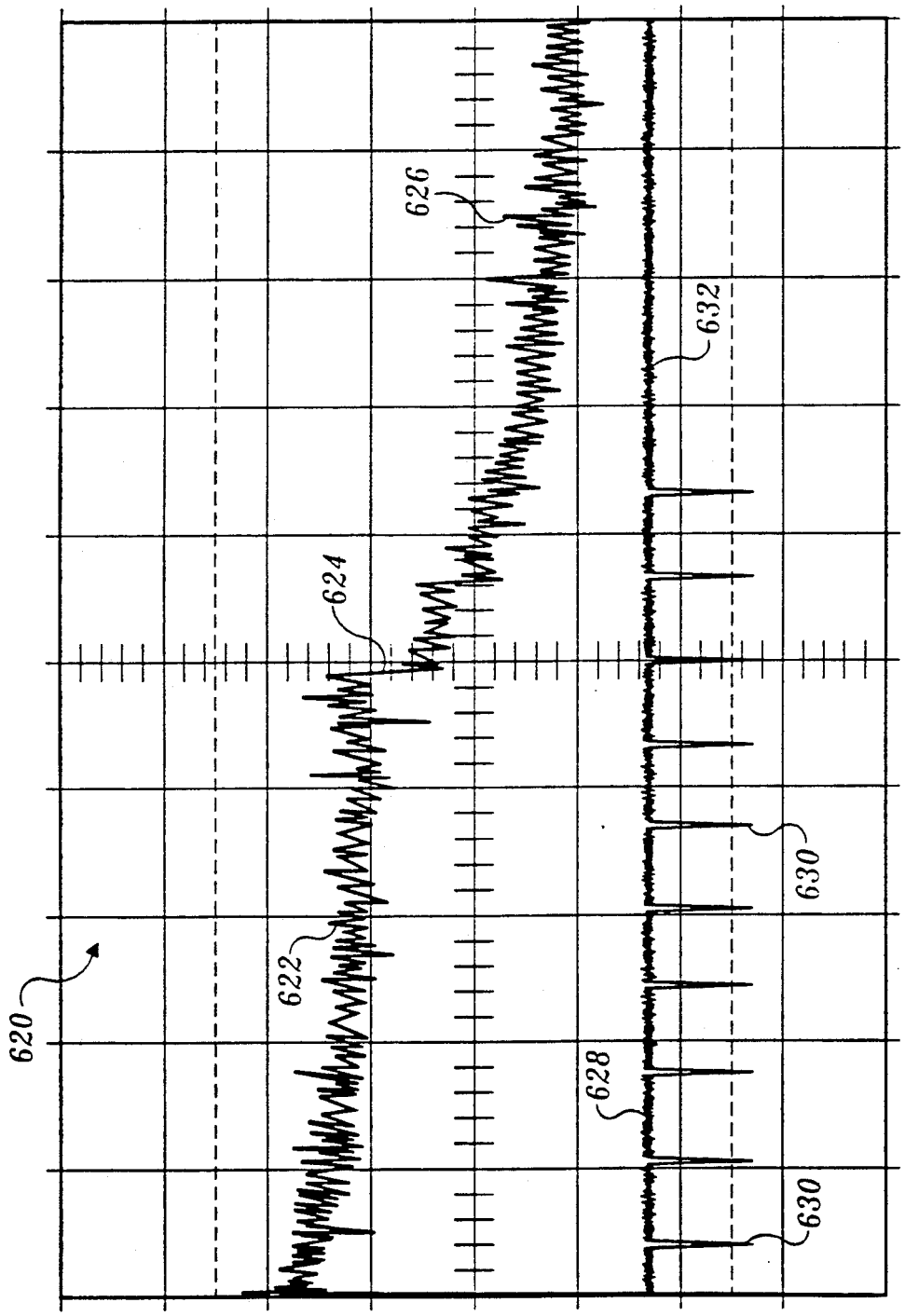
FIG. 17 graphically shows an oscilloscope trace of the output signal from the proximal pressure sensor when the volumetric pump is operating at a delivery rate of about 6 ml/hr., illustrating the change that occurs in this signal when the proximal portion of the flexible tube carrying fluid through the volumetric pump is closed with a roller clamp; a second trace shows the pulse produced each time that the cam assembly passes its home position.

FIG. 17 also shows a typical proximal pressure sensor output signal oscilloscope trace 620 and a trace 628, which represents the cam assembly reed switch output signal. In FIG. 17, volumetric pump 30 is again operating at a nominal fluid flow rate of 6 milliliters per hour; however, seven minutes after the pumping session is initiated, a roller clamp (not shown) is applied to close proximal portion 34a of the flexible tubing. It should be apparent that prior to the closure of the clamp, the average proximal pressure signal amplitude (at reference numeral 622) is relatively higher than the closure (at reference numeral 624). The proximal pressure signal rapidly decreases following the closure of the clamp to a level shown at reference numeral 626. Furthermore, once the proximal occlusion is detected, volumetric pump 30 ceases operation, as is evident from the cessation of pulses 630 that occurs approximately three minutes after the roller clamp was applied to the proximal portion of the flexible tubing. Thereafter, pulses 630 are absent in the portion of the signal produced by the cam assembly reed switch, yielding substantially a flat trace 632 on the lower right side of FIG. 17.

Figure 18:
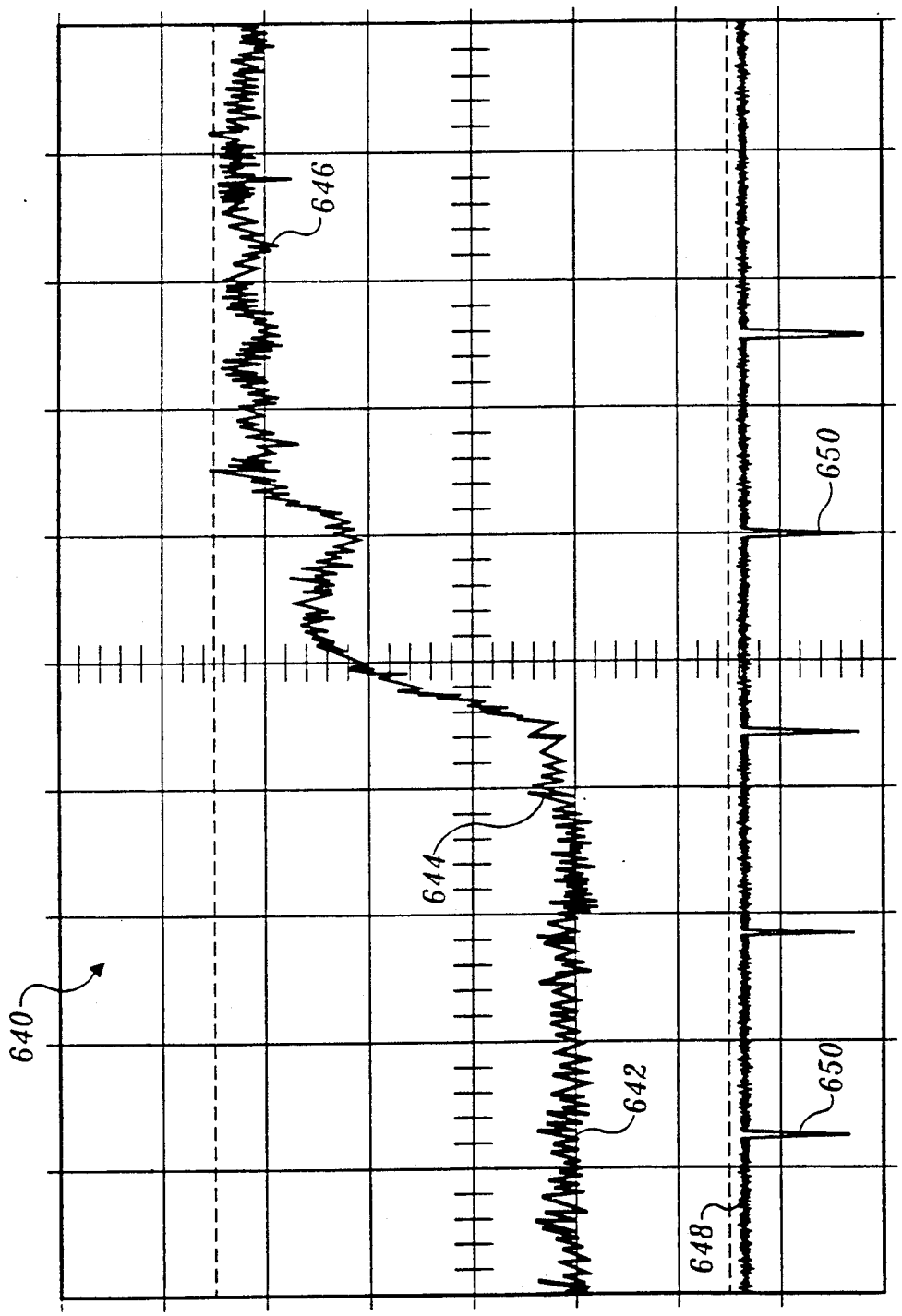
FIG. 18 graphically shows an oscilloscope trace of the output signal from the distal pressure sensor in the volumetric pump operating at a flow rate of 125 ml/hr., illustrating the change that occurs in this signal when the distal portion of the flexible tube is pinched closed; also shown are the pulses produced as the cam assembly passes its home position with each pump cycle.

In FIG. 18, an oscilloscope trace 640 representing the output signal from the distal pressure sensor is shown. A relatively low average amplitude for the signal is obtained (at reference numeral 642) prior to the distal portion 34c of the flexible tubing being pinched closed at approximately the midpoint of trace 640, at reference numeral 644. Thereafter, the distal pressure signal amplitude rises to a relatively higher average level, as represented by reference numeral 646. Also shown in FIG. 18 is an oscilloscope trace 648 representing the output signal from the reed switch that monitors the home position of cam assembly 142. Trace 648 includes a plurality of spaced-apart pulses 650, each produced when cam assembly 142 passes its home position. In FIG. 18, volumetric pump 30 is operating at a nominal flow rate of 125 milliliters per hour so that each pumping cycle is approximately 0.35 seconds in duration.

As will be evident from FIGS. 16 through 18, detection of proximal and distal occlusions requires rejection of artifacts and averaging of the signal over time to avoid false alarms. The pressures in the proximal and distal portions of the volumetric pump are dynamically varying parameters. The occlusion detection method and apparatus of the present invention avoids dynamic variations in the fluid pressure by sensing the pressures at predefined intervals of time during the pumping cycle when those pressures have changed and by rejecting noise and other artifacts that would otherwise interfere with the determination of an occlusion. Accordingly, the method and apparatus used for detecting such occlusions are more complex than might at first seem necessary. By properly compensating for relaxation of the flexible tubing and for other artifacts in the signals, a reliable occlusion detection system and method are thus provided.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. In a pump that forces a fluid to flow through an integral flexible line, from an inlet portion to an outlet portion of the flexible line, apparatus for detecting at least a partial occlusion of at least one of the inlet and the outlet portions, comprising:
   a. a pressure sensor mechanically coupled to said one of the inlet and outlet portions, the pressure sensor producing a signal corresponding to a fluid pressure within said one portion without being exposed to the fluid within said portion;
   b. a flexure assembly that mechanically couples the pressure sensor to said one portion; and
   c. control means, electronically connected to receive the signal from the pressure sensor, for monitoring the fluid pressure within said one portion at a predefined time during a pump cycle selected to minimize noise in the signal, the control means including means for rejecting a residual noise in the signal and for determining if an occlusion of said one portion has occurred in response to the magnitude of the signal.

2. The apparatus of claim 1, wherein the pressure sensor comprises a strain gauge that responds to a cross-sectional deflection of said one portion caused by the fluid pressure within said one portion, the deflection of said one portion causing the flexure assembly to bend, the signal produced by the strain gauge corresponding to the deflection and, thus, to the fluid pressure within said portion.

3. The apparatus of claim 1, further comprising a second pressure sensor mechanically coupled to the other of the inlet and the outlet portions, which produces a signal corresponding to a fluid pressure within said other portion without being exposed to the fluid within the portion, the second pressure sensor being mechanically coupled by the flexure assembly to said other portion.

4. The apparatus of claim 3, wherein the control means are connected to receive the signal produced by the second pressure sensor and detect an occlusion in said other portion as a function of a magnitude of said signal produced by the second pressure sensor.

5. The apparatus of claim 3, wherein the second pressure sensor comprises a strain gauge that monitors a cross-sectional deflection of said other portion caused by the fluid pressure within said other portion by monitoring strain in the flexure assembly, deflection of said other portion causing the flexure assembly to bend, so that the signal produced by the strain gauge corresponds to the fluid pressure within said other portion.

6. The apparatus of claim 1, wherein said one portion is the inlet portion, and the control means detect an occlusion of the inlet portion if the signal is less than a predefined value.

7. The apparatus of claim 1, wherein said one portion is the outlet portion, and the control means detect an occlusion of the outlet portion if the signal is greater than a predefined value.

8. The apparatus of claim 1, wherein the control means determine a baseline pressure based upon a weighted average of the fluid pressure as sensed at the predetermined time during consecutive pump cycles, to compensate for variations in the deflection of said one portion that are independent of an occlusion of said one portion and produce the residual noise in the signal.

9. The apparatus of claim 8, wherein the means for determining detect an occlusion if the fluid pressure deviates from the baseline pressure by more than a predefined amount during a predefined number of consecutive pump cycles.

10. Apparatus for detecting at least a partial occlusion of either an inlet line or of an outlet line of a pump, comprising:
  a. a first pressure sensor that is mechanically coupled to the inlet line to sense a fluid pressure therein without exposure to the fluid within the inlet line, producing a first signal indicative of that fluid pressure;
  b. a second pressure sensor that is mechanically coupled to the outlet line to sense a fluid pressure therein without exposure to the fluid within the outlet line, producing a second signal indicative of that fluid pressure;
  c. a flexure assembly that supports a first block and a second block and maintains the first and the second blocks in contact with the inlet line and the outlet line, respectively, as the flexure assembly bends, the flexure assembly thus mechanically coupling the first pressure sensor to the inlet line and the second pressure sensor to the outlet line, respectively; and
  d. control means, connected to receive the first and the second signals, for monitoring the fluid pressure within the inlet and outlet lines, the control means including detection means for determining whether an occlusion of the inlet line or of the outlet line has occurred, as a function of the first and the second signals.

11. The apparatus of claim 10, wherein the first and the second pressure sensors each comprise strain gauges that respond to a cross-sectional deflection of the inlet and the outlet lines, respectively, caused by the fluid pressure within the lines, the first signal and the second signal that are produced by the strain gauges corresponding to the deflection and, thus, to the fluid pressures within the inlet and the outlet lines, the strain gauges being mounted on the flexure assembly and being sensitive to stress in different portions of the flexure assembly, so as to independently respond to the fluid pressures in the inlet line and in the outlet line.

12. The apparatus of claim 10, wherein the control means determine a baseline pressure for the inlet line and a baseline pressure for the outlet line, each baseline pressure being dependent upon a weighted average of the fluid pressure within the corresponding inlet or outlet line, as sensed at predetermined times during consecutive pump cycles, the predetermined times being selected to compensate for variations in the deflection of the inlet line and the outlet line that are independent of an occlusion and thus represent noise.

13. The apparatus of claim 12, wherein the detection means detect an occlusion of the inlet line if the fluid pressure within the inlet line deviates from its baseline pressure by more than a predefined amount during a predefined number of consecutive pump cycles.

14. The apparatus of claim 12, wherein the detection means detect an occlusion of the outlet line if the fluid pressure within the outlet line deviates from its baseline pressure by more than a predefined amount during a predefined number of consecutive pump cycles.

15. The apparatus of claim 12, wherein the detection means determine a pressure delta baseline that is a function of a difference between the baseline pressures of the inlet line and the outlet line and use the pressure delta baseline as a reference in determining that an absolute occlusion of the outlet line has occurred.

16. The apparatus of claim 15, wherein the control means include memory means for storing the pressure delta baseline, the detection means being operative to compare a present value of the pressure delta baseline with a previous value of the pressure delta baseline that was stored by the memory means, to detect the absolute occlusion of the outlet line.

17. The apparatus of claim 10, further comprising interface means for enabling an operator to select a reference pressure used by the detection means in detecting an occlusion of the inlet line or of the outlet line.

18. The apparatus of claim 10, wherein the detection means compensate for changes in the cross-sectional deflection of the inlet line and of the outlet line over time, due to changes in an elasticity of said lines under pressure.

19. A method for detecting at least a partial occlusion of either an inlet line or an outlet line of a pump during a pumping cycle, comprising:
  a. at a predefined first time interval during the pumping cycle, mechanically sensing a fluid pressure at the inlet of the pump without directly contacting a fluid within the inlet line, the predefined time interval being selected so as to minimize noise in a signal produced thereby that is indicative of said fluid pressure;
  b. at a predefined second time interval during the pumping cycle, mechanically sensing a fluid pressure at the outlet of the pump without directly contacting a fluid within the outlet line, the predefined time being selected so as to minimize noise in a signal produced thereby that is indicative of said fluid pressure:

c. rejecting residual noise in the signals indicative of fluid pressure pressure in the inlet line and in the outlet line, respectively; and d. determining whether an occlusion of the inlet line or of the outlet line has occurred, as a function of the signals indicative of fluid pressure in the inlet line and in the outlet line of the pump, respectively.

20. The method of claim 19, wherein the steps of sensing fluid pressure at the inlet line and at the outlet line of the pump, respectively, comprise the steps of sensing a cross-sectional deflection of the inlet line and of the outlet line caused by the fluid pressure within said lines.

21. The method of claim 19, further comprising the steps of determining a baseline pressure for the inlet line and determining a baseline pressure for the outlet line, the baseline pressures for the inlet line being based upon a weighted average of the fluid pressure therein and the baseline pressure for the outlet line being based upon a weighted average of the fluid pressure therein and the baseline pressure for the outlet line being based upon a weighted average of the fluid pressure therein, as sensed at the predetermined time intervals during consecutive pump cycles, so that variations in the deflection of the inlet line and the outlet line that are independent of their occlusion are compensated.

22. The method of claim 21, wherein an occlusion of the inlet line is detected if the fluid pressure within the inlet line deviates from its baseline pressure by more than a predefined amount during each of a predefined number of consecutive pump cycles.

23. The method of claim 21, where an occlusion of the outlet line is detected if the fluid pressure within the outlet line deviates from its baseline pressure by more than a predefined amount during each of a predefined number of consecutive pump cycles.

24. The method of claim 21, further comprising the steps of determining a pressure delta baseline that is a function of a difference between the baseline pressures of the inlet line and the outlet line; and using the pressure delta baseline as a reference in determining whether an absolute occlusion of the outlet line has occurred.

* * * * *

UNITED STATES PATENT AND TRADEMARK OFFICE
CERTIFICATE OF CORRECTION

PATENT NO. : 5,116,203  
DATED : May 26, 1992  
INVENTOR(S) : V. R. Natwick et al.

Page 1 of 2

It is certified that error appears in the above-identified patent and that said Letters Patent is hereby corrected as shown below:

On the title page, Item [56]:

Insert --
| | | | |
|---|---|---|---|
| 2,412,397 | 12/1946 | Harper | 103/148 |
| 3,609,069 | 09/1971 | Martinelli | 417/474 |
| 4,277,226 | 07/1981 | Archibald | 417/38 |
| 4,302,164 | 11/1981 | Manella | 417/474 |
| 4,391,600 | 07/1983 | Archibald | 604/153 |
| 4,479,797 | 10/1984 | Kobayashi et al. | 604/153 |
| 4,559,038 | 12/1985 | Berg et al. | 604/153 |
| 4,650,469 | 03/1987 | Berg et al. | 604/131 |
| 4,653,987 | 03/1987 | Tsuji et al. | 417/360 |
| 4,690,673 | 09/1987 | Bloomquist | 604/67 |
| 4,728,265 | 03/1988 | Cannon | 417/363-- |

| Column | Line | |
|---|---|---|
| 10 | 27 | "contact" should read --contacts-- |
| 10 | 30 | "blcok" should read --block-- |
| 11 | 63 | "oppsite" should read --opposite-- |
| 17 | 19 | "procees" should read --proceeds-- |
| 19 | 17 | "of" should read --or-- |

UNITED STATES PATENT AND TRADEMARK OFFICE
CERTIFICATE OF CORRECTION

PATENT NO. : 5,116,203

DATED : May 26, 1992

INVENTOR(S) : V. R. Natwick et al.

It is certified that error appears in the above-identified patent and that said Letters Patent is hereby corrected as shown below:

| COLUMN | LINES | |
|---|---|---|
| 23 | 7 | delete "pressure" (second occurrence) |
| 23 & 24 | 25-2 | delete "and the baseline pressure for the outlet line being based upon a weighted average of the fluid pressure therein" |

Signed and Sealed this

Twenty-first Day of September, 1993

Attest:

BRUCE LEHMAN

Attesting Officer

Commissioner of Patents and Trademarks